(12) United States Patent  (10) Patent No.: US 8,323,241 B2
Salahieh et al.  (45) Date of Patent: Dec. 4, 2012

(54) STEERABLE MEDICAL DELIVERY DEVICES AND METHODS OF USE

(75) Inventors: Amr Salahieh, Saratoga, CA (US); Jonah Lepak, Santa Cruz, CA (US); Emma Leung, Sunnyvale, CA (US); Tom Saul, El Granada, CA (US); Jean-Pierre Dueri, Stockton, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 142 days.

(21) Appl. No.: 12/823,049

(22) Filed: Jun. 24, 2010

(65) Prior Publication Data

US 2010/0331776 A1 Dec. 30, 2010

Related U.S. Application Data

(60) Provisional application No. 61/220,160, filed on Jun. 24, 2009, provisional application No. 61/220,163, filed on Jun. 24, 2009, provisional application No. 61/232,362, filed on Aug. 7, 2009.

(51) Int. Cl.
*A61M 31/00* (2006.01)

(52) U.S. Cl. ................................... 604/95.04
(58) Field of Classification Search ............... 604/95.04, 604/523, 525, 528
See application file for complete search history.

(56) References Cited

U.S. PATENT DOCUMENTS

| 4,031,713 A | 6/1977 | Driver |
| 4,353,358 A | 10/1982 | Emerson |
| 4,547,193 A | 10/1985 | Rydell |
| 4,580,551 A | 4/1986 | Siegmund et al. |
| 4,634,432 A | 1/1987 | Kocak |
| 4,692,139 A | 9/1987 | Stiles |
| 4,726,382 A | 2/1988 | Boehmer et al. |
| 4,890,623 A | 1/1990 | Cook et al. |
| 4,911,148 A | 3/1990 | Sosnowski et al. |
| 5,010,895 A | 4/1991 | Maurer et al. |
| 5,041,089 A | 8/1991 | Mueller et al. |
| 5,052,404 A | 10/1991 | Hodgson |
| 5,069,674 A | 12/1991 | Fearnot et al. |
| 5,180,376 A | 1/1993 | Fischell |
| 5,209,741 A | 5/1993 | Spaeth |
| 5,228,441 A | 7/1993 | Lundquist |
| 5,228,442 A | 7/1993 | Imran |
| 5,235,964 A | 8/1993 | Abenaim |
| 5,284,128 A | 2/1994 | Hart |
| 5,299,562 A | 4/1994 | Heckele et al. |
| 5,309,910 A | 5/1994 | Edwards et al. |
| 5,311,866 A | 5/1994 | Kagan et al. |
| 5,315,996 A | 5/1994 | Lundquist |
| 5,322,064 A | 6/1994 | Lundquist |

(Continued)

FOREIGN PATENT DOCUMENTS

DE 4104092 A1 8/1991

(Continued)

OTHER PUBLICATIONS

Salahieh et al.; U.S. Appl. No. 13/106,658 entitled "Low Profile Electrode Assembly," filed May 12, 2011.

(Continued)

*Primary Examiner* — Nicholas Lucchesi
*Assistant Examiner* — Jason Flick
(74) *Attorney, Agent, or Firm* — Shay Glenn LLP

(57) ABSTRACT

Steerable medical delivery devices and their methods of use.

34 Claims, 18 Drawing Sheets

U.S. PATENT DOCUMENTS

| | | |
|---|---|---|
| 5,325,845 A | 7/1994 | Adair |
| 5,329,923 A | 7/1994 | Lundquist |
| 5,334,145 A | 8/1994 | Lundquist et al. |
| 5,343,860 A | 9/1994 | Metzger et al. |
| 5,366,490 A | 11/1994 | Edwards et al. |
| 5,370,675 A | 12/1994 | Edwards et al. |
| 5,372,587 A | 12/1994 | Hammerslag et al. |
| 5,381,782 A | 1/1995 | DeLaRama et al. |
| 5,385,544 A | 1/1995 | Edwards et al. |
| 5,391,200 A | 2/1995 | KenKnight et al. |
| 5,395,329 A | 3/1995 | Fleischhacker et al. |
| 5,409,453 A | 4/1995 | Lundquist et al. |
| 5,421,819 A | 6/1995 | Edwards et al. |
| 5,435,805 A | 7/1995 | Edwards et al. |
| 5,443,470 A | 8/1995 | Stern et al. |
| 5,454,787 A | 10/1995 | Lundquist |
| 5,456,662 A | 10/1995 | Edwards et al. |
| 5,470,308 A | 11/1995 | Edwards et al. |
| 5,470,309 A | 11/1995 | Edwards et al. |
| 5,480,382 A | 1/1996 | Hammerslag et al. |
| 5,505,730 A | 4/1996 | Edwards |
| 5,515,848 A | 5/1996 | Corbett, III et al. |
| 5,524,338 A | 6/1996 | Martyniuk et al. |
| 5,540,679 A | 7/1996 | Fram et al. |
| 5,558,672 A | 9/1996 | Edwards et al. |
| 5,562,720 A | 10/1996 | Stern et al. |
| 5,569,241 A | 10/1996 | Edwards |
| 5,571,088 A | 11/1996 | Lennox et al. |
| 5,573,520 A | 11/1996 | Schwartz et al. |
| 5,575,772 A | 11/1996 | Lennox |
| 5,575,788 A | 11/1996 | Baker et al. |
| 5,609,606 A | 3/1997 | O'Boyle |
| 5,630,837 A | 5/1997 | Crowley |
| 5,681,308 A | 10/1997 | Edwards et al. |
| 5,715,825 A | 2/1998 | Crowley |
| 5,718,701 A | 2/1998 | Shai et al. |
| 5,735,846 A | 4/1998 | Panescu et al. |
| 5,741,429 A | 4/1998 | Donadio, III et al. |
| 5,769,846 A | 6/1998 | Edwards et al. |
| 5,779,698 A | 7/1998 | Clayman et al. |
| 5,836,874 A | 11/1998 | Swanson et al. |
| 5,846,196 A | 12/1998 | Siekmeyer et al. |
| 5,846,238 A | 12/1998 | Jackson et al. |
| 5,846,239 A | 12/1998 | Swanson et al. |
| 5,853,411 A | 12/1998 | Whayne et al. |
| 5,860,974 A | 1/1999 | Abele |
| 5,871,483 A | 2/1999 | Jackson et al. |
| 5,879,348 A | 3/1999 | Owens et al. |
| 5,888,577 A | 3/1999 | Griffin, III et al. |
| 5,904,651 A | 5/1999 | Swanson et al. |
| 5,938,660 A | 8/1999 | Swartz et al. |
| 5,961,513 A | 10/1999 | Swanson et al. |
| 5,991,650 A | 11/1999 | Swanson et al. |
| 6,004,269 A | 12/1999 | Crowley et al. |
| 6,012,457 A | 1/2000 | Lesh |
| 6,024,740 A | 2/2000 | Lesh et al. |
| 6,052,607 A | 4/2000 | Edwards et al. |
| 6,053,922 A | 4/2000 | Krause et al. |
| 6,123,718 A | 9/2000 | Tu et al. |
| 6,142,993 A | 11/2000 | Whayne et al. |
| 6,163,726 A | 12/2000 | Wolf |
| 6,164,283 A | 12/2000 | Lesh |
| 6,206,912 B1 | 3/2001 | Goldsteen et al. |
| 6,246,914 B1 | 6/2001 | de la Rama et al. |
| 6,292,689 B1 | 9/2001 | Wallace et al. |
| 6,402,746 B1 | 6/2002 | Whayne et al. |
| 6,460,545 B2 | 10/2002 | Kordis |
| 6,500,174 B1 | 12/2002 | Maguire et al. |
| 6,511,471 B2 | 1/2003 | Rosenman et al. |
| 6,514,249 B1 | 2/2003 | Maguire et al. |
| 6,551,271 B2 | 4/2003 | Nguyen |
| 6,558,378 B2 | 5/2003 | Sherman et al. |
| 6,572,609 B1 | 6/2003 | Farr et al. |
| 6,572,612 B2 | 6/2003 | Stewart et al. |
| 6,585,718 B2 | 7/2003 | Hayzelden et al. |
| 6,595,989 B1 | 7/2003 | Schaer |
| 6,635,054 B2 | 10/2003 | Fjield et al. |
| 6,652,515 B1 | 11/2003 | Maguire et al. |
| 6,660,002 B1 | 12/2003 | Edwards et al. |
| 6,685,679 B2 | 2/2004 | Merdan |
| 6,736,811 B2 | 5/2004 | Panescu et al. |
| 6,743,226 B2 | 6/2004 | Cosman et al. |
| 6,749,560 B1 | 6/2004 | Konstorum et al. |
| 6,771,996 B2 | 8/2004 | Bowe et al. |
| 6,780,183 B2 | 8/2004 | Jimenez, Jr. et al. |
| 6,808,524 B2 | 10/2004 | Lopath et al. |
| 6,814,730 B2 | 11/2004 | Li |
| 6,869,431 B2 | 3/2005 | Maguire et al. |
| 6,872,183 B2 | 3/2005 | Sampson et al. |
| 6,872,206 B2 | 3/2005 | Edwards et al. |
| 6,911,027 B1 | 6/2005 | Edwards et al. |
| 6,942,657 B2 | 9/2005 | Sinofsky et al. |
| 6,978,174 B2 | 12/2005 | Gelfand et al. |
| 6,979,312 B2 | 12/2005 | Shimada |
| 7,001,369 B2 | 2/2006 | Griffin et al. |
| 7,048,733 B2 | 5/2006 | Hartley et al. |
| 7,101,362 B2 | 9/2006 | Vanney |
| 7,105,003 B2 | 9/2006 | Hiltebrandt |
| 7,115,122 B1 | 10/2006 | Swanson et al. |
| 7,137,395 B2 | 11/2006 | Fried et al. |
| 7,150,745 B2 | 12/2006 | Stern et al. |
| 7,162,303 B2 | 1/2007 | Levin et al. |
| 7,207,984 B2 | 4/2007 | Farr et al. |
| 7,226,448 B2 | 6/2007 | Bertolero et al. |
| 7,232,437 B2 | 6/2007 | Berman et al. |
| 7,238,179 B2 | 7/2007 | Brucker et al. |
| 7,238,180 B2 | 7/2007 | Mester et al. |
| 7,267,674 B2 | 9/2007 | Brucker et al. |
| 7,276,062 B2 | 10/2007 | McDaniel et al. |
| 7,286,866 B2 | 10/2007 | Okerlund et al. |
| 7,291,146 B2 | 11/2007 | Steinke et al. |
| 7,310,150 B2 | 12/2007 | Guillermo et al. |
| 7,346,381 B2 | 3/2008 | Okerlund et al. |
| 7,357,796 B2 | 4/2008 | Farr et al. |
| 7,365,859 B2 | 4/2008 | Yun et al. |
| 7,366,376 B2 | 4/2008 | Shishkov et al. |
| 7,371,231 B2 | 5/2008 | Rioux et al. |
| 7,382,949 B2 | 6/2008 | Bouma et al. |
| 7,396,355 B2 | 7/2008 | Goldman et al. |
| 7,402,151 B2 * | 7/2008 | Rosenman et al. ........ 604/95.05 |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,469,700 B2 | 12/2008 | Baran |
| 7,472,705 B2 | 1/2009 | Baran |
| 7,473,251 B2 | 1/2009 | Knowlton et al. |
| 7,481,808 B2 | 1/2009 | Koyfman et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,519,096 B2 | 4/2009 | Bouma et al. |
| 7,529,393 B2 | 5/2009 | Peszynski et al. |
| 7,538,859 B2 | 5/2009 | Tearney et al. |
| 7,617,005 B2 | 11/2009 | Demarais et al. |
| 7,620,451 B2 | 11/2009 | Demarais et al. |
| 7,653,438 B2 | 1/2010 | Deem et al. |
| 7,669,309 B2 | 3/2010 | Johnson et al. |
| 7,691,095 B2 | 4/2010 | Bednarek et al. |
| 7,711,148 B2 | 5/2010 | Slabaugh et al. |
| 7,756,583 B2 | 7/2010 | Demarais et al. |
| 7,853,333 B2 | 12/2010 | Demarais |
| 2002/0002384 A1 | 1/2002 | Gilson et al. |
| 2002/0095147 A1 | 7/2002 | Shadduck |
| 2003/0236443 A1 | 12/2003 | Cespedes et al. |
| 2004/0102719 A1 | 5/2004 | Keith et al. |
| 2005/0131343 A1 * | 6/2005 | Abrams et al. ............ 604/95.04 |
| 2005/0159728 A1 | 7/2005 | Armour et al. |
| 2006/0041277 A1 | 2/2006 | Deem et al. |
| 2006/0100618 A1 | 5/2006 | Chan et al. |
| 2006/0100687 A1 | 5/2006 | Fahey et al. |

| | | |
|---|---|---|
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0241564 A1* | 10/2006 | Corcoran et al. ............. 604/523 |
| 2006/0247701 A1 | 11/2006 | Zacouto |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0078507 A1 | 4/2007 | Zacouto |
| 2007/0112422 A1 | 5/2007 | Dehdashtian |
| 2007/0129760 A1 | 6/2007 | Demarais et al. |
| 2007/0135875 A1 | 6/2007 | Demarais et al. |
| 2007/0225634 A1 | 9/2007 | Ferren et al. |
| 2007/0244501 A1 | 10/2007 | Horn et al. |
| 2008/0021405 A1 | 1/2008 | Jacobsen et al. |
| 2008/0188912 A1 | 8/2008 | Stone et al. |
| 2008/0275445 A1 | 11/2008 | Kelly et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0227885 A1 | 9/2009 | Lowery et al. |
| 2009/0240249 A1 | 9/2009 | Chan et al. |
| 2009/0254142 A1 | 10/2009 | Edwards et al. |
| 2009/0312754 A1 | 12/2009 | Lenihan et al. |
| 2010/0204560 A1 | 8/2010 | Salahieh et al. |
| 2012/0116438 A1 | 5/2012 | Salahieh et al. |

FOREIGN PATENT DOCUMENTS

| | | |
|---|---|---|
| EP | 0637943 B1 | 4/1998 |
| EP | 0723467 B1 | 4/2002 |
| EP | 0693955 B1 | 1/2003 |
| EP | 1382366 A1 | 1/2004 |
| WO | WO 99/00060 A1 | 1/1999 |
| WO | WO 00/66014 A1 | 11/2000 |
| WO | WO 2009/067695 A1 | 5/2009 |
| WO | WO 2009/132137 A1 | 10/2009 |

OTHER PUBLICATIONS

Drafts, Bill; Acoustic wave technology sensors; Sensors Weekly (Questex Media Group); 10 pgs.; Oct. 1, 2000 (http://www.sensorsmag.com/sensors/acoustic-ultrasound/acoustic-wave-technology-sensors-936).

Salahieh et al.; U.S. Appl. No. 13/071,436 entitled "Intravascular Tissue Disruption," filed Mar. 24, 2011.

* cited by examiner

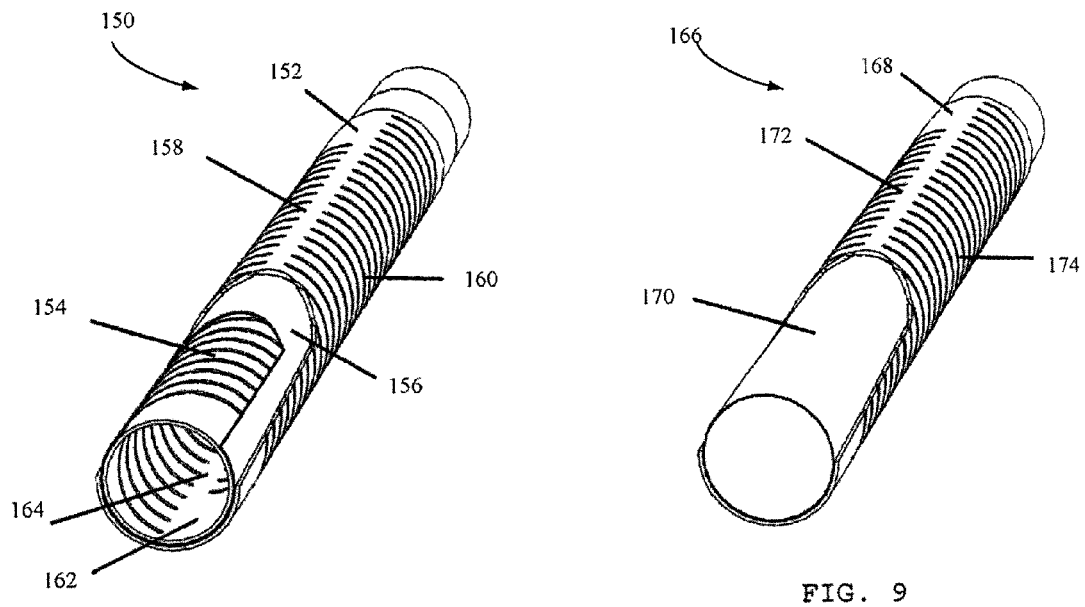
FIG. 8
FIG. 9
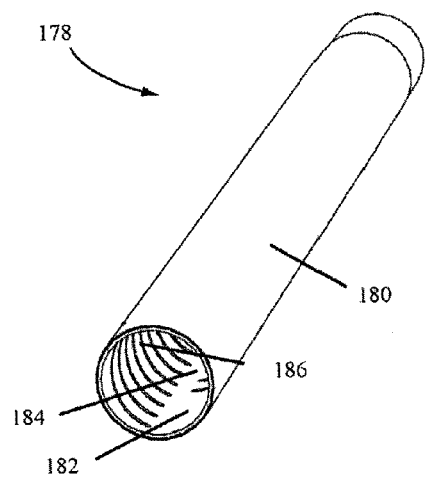
FIG. 10

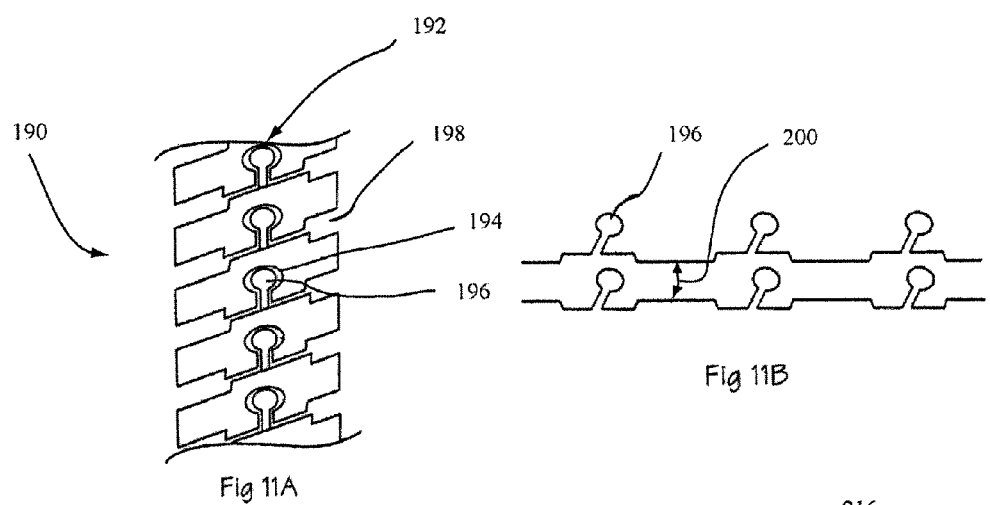
Fig 11A
Fig 11B
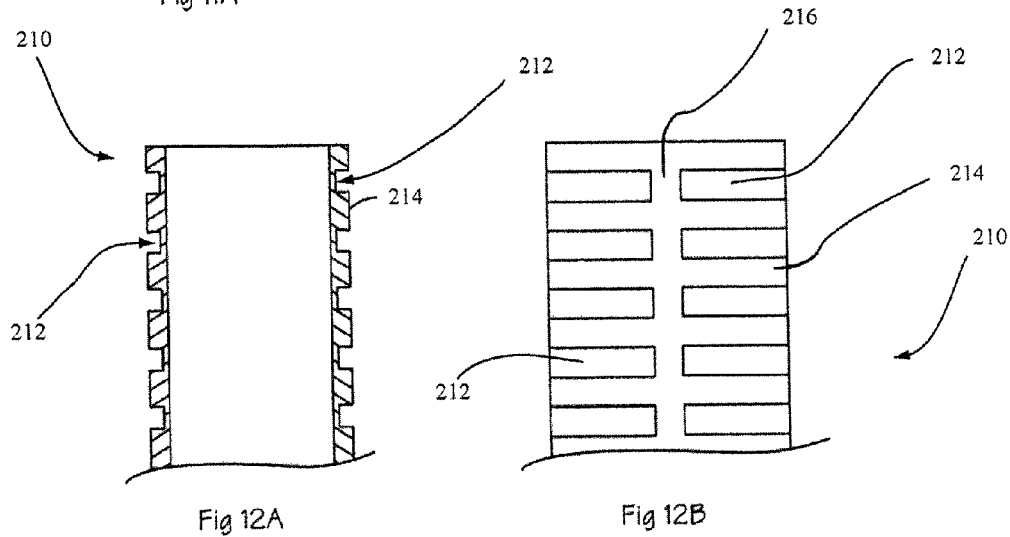
Fig 12A
Fig 12B

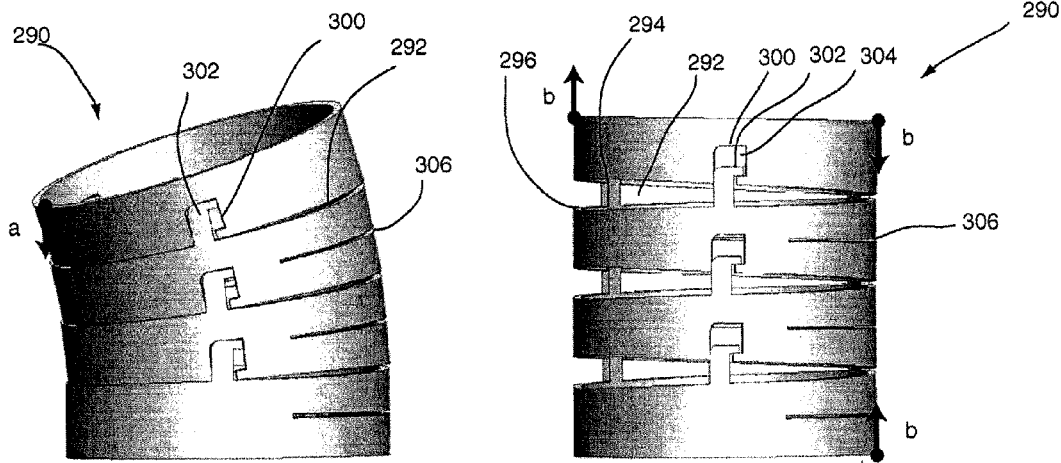
Fig 16a
Fig 16b
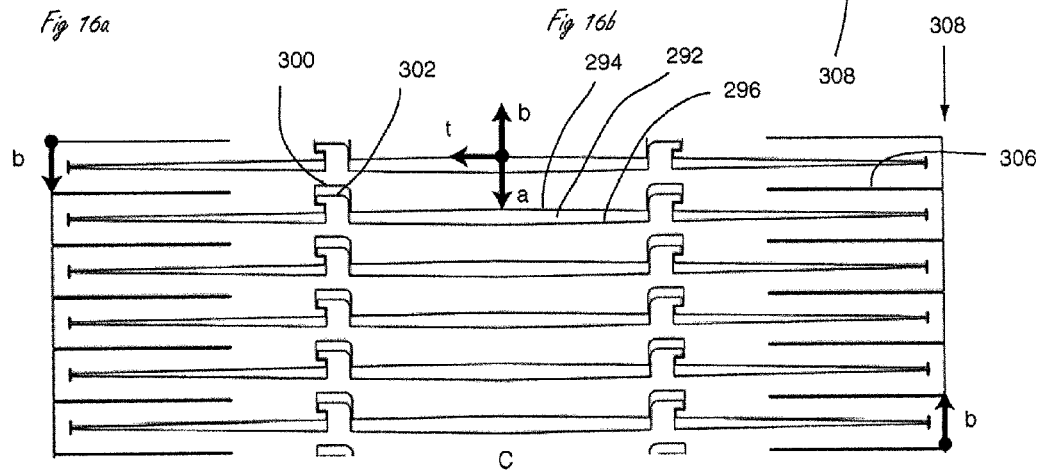
Fig 16c
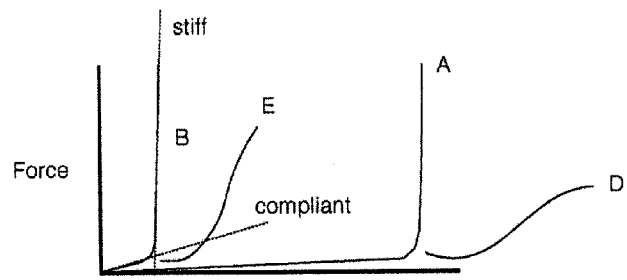
Fig 17

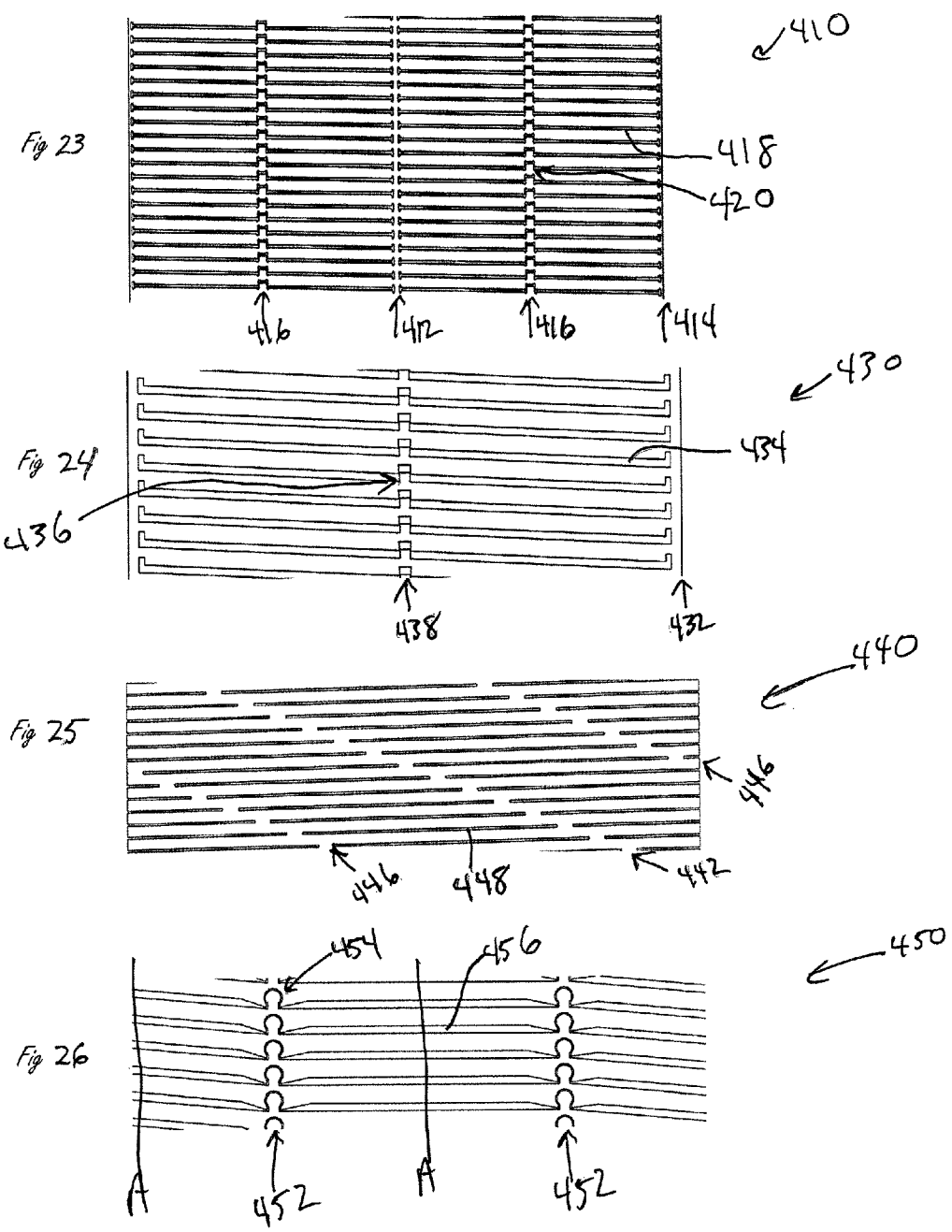

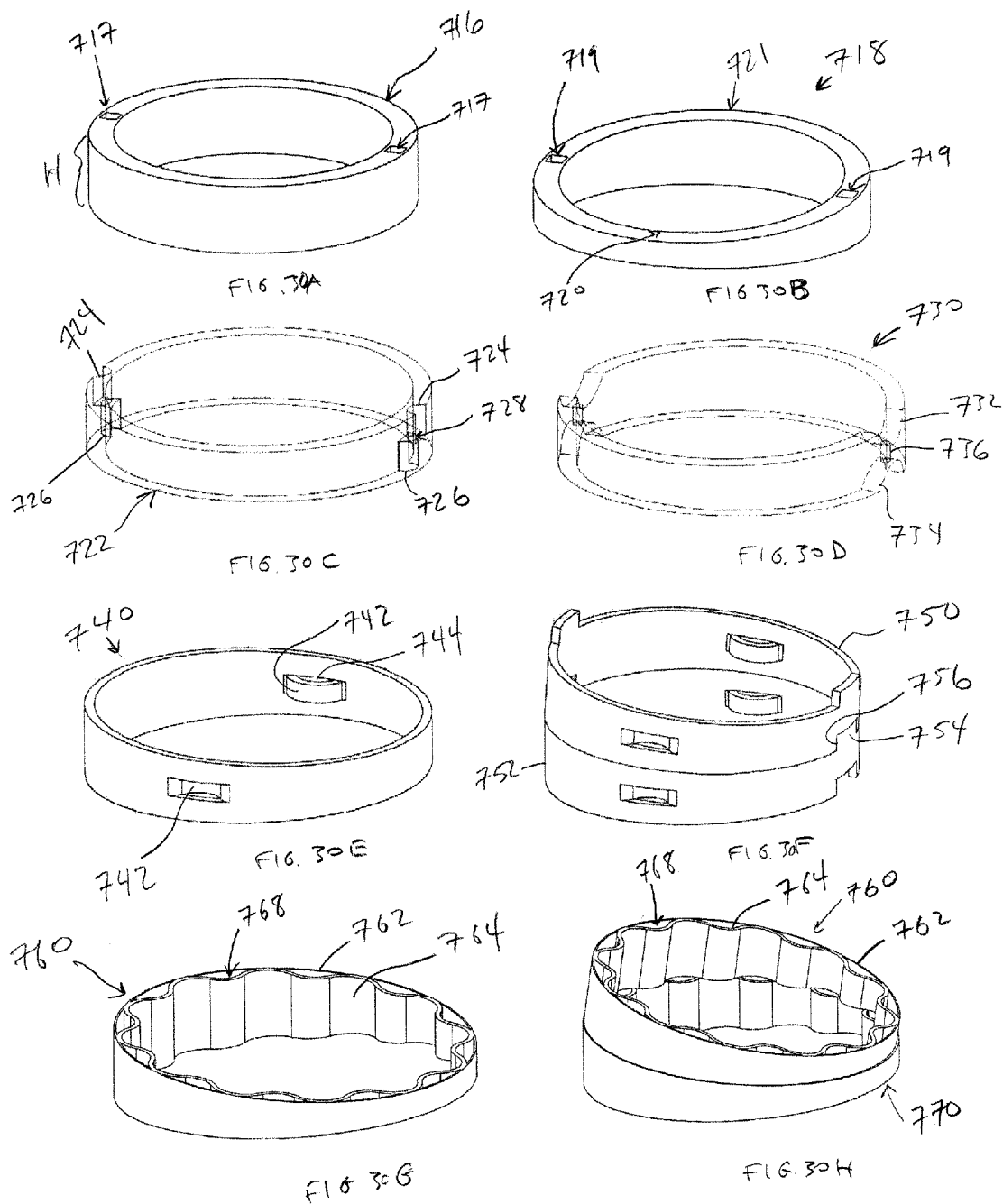

STEERABLE MEDICAL DELIVERY DEVICES AND METHODS OF USE

CROSS-REFERENCE

This application claims the benefit of U.S. Provisional Application No. 61/220,160, filed Jun. 24, 2009; U.S. Provisional Application No. 61/220,163, filed Jun. 24, 2009; and U.S. Provisional Application No. 61/232,362, filed Aug. 7, 2009, all of which are incorporated by reference herein.

BACKGROUND OF THE INVENTION

Delivery devices are used to deliver, or guide, medical devices or instruments to a target location within a subject. The delivery devices provide access to target locations within the body where, for example, diagnostic, therapeutic, and interventional procedures are required. Access via these devices is generally minimally invasive, and can be either percutaneous, or through natural body orifices. The access can require providing a guiding path through a body lumen, such as, for example without limitation, a blood vessel, an esophagus, a trachea and adjoining bronchia, ducts, any portion of the gastro intestinal tract, and the lymphatics. Once the delivery device has provided access to the target location, the delivery device is then used to guide the medical device or instrument to perform the diagnostic, therapeutic, or interventional procedure. An example of such a delivery device is a guide catheter, which may be delivered by steering it to its required destination, tracking it along a previously delivered guide wire, or both. The list of components being delivered for use percutaneously is large and rapidly growing.

Minimal outer dimensions of these delivery devices are important for minimizing the injury associated with delivery. Minimizing the wall thickness of the delivery device provides additional space for the medical device to be guided, while minimizing the injury associated with entry into the subject and the closure needed. Flexibility of the delivery device is important in allowing the guiding device to track or be steered to its target destination along tortuous paths while minimizing injury to the intervening tissues. The delivery device also needs to have compressive and tensile properties sufficient to support its delivery to the target site. When tracking around bends in the body, any kinks created in the guiding device can create an obstruction to the delivery of the medical device. When used as a steerable device, the distal end of the delivery device is preferably deflectable over a range of bend radii and responsive to the steering controls. The delivery device also should support torque transmitted from the handle to the distal region.

Once the delivery device is in place the delivery device preferably also supports torque around a distal bend such that the medical device may be rotated into position while sustaining some contact loads. Additionally, once in place the guiding device preferably is sufficiently stiff to support and guide the medical device to its target destination. The guiding device should also remain stable and not shift from one state of equilibrium to another either spontaneously or under the influence of forces being imparted to it from the delivery of the medical device or its own control mechanisms. As the delivery device often travels down fluid-filled lumens such as, for example without limitation, blood vessels, it should additionally incorporate a seal against fluids impinging upon its periphery and another at its distal end which interfaces with the medical device to maintain a seal around the delivery device.

There exists a need for improved steerable delivery devices and guiding medical devices.

SUMMARY OF THE INVENTION

One aspect of the disclosure is a steerable medical delivery device. The device includes a steerable portion comprising a first tubular member and a second tubular member, wherein one of the first and second tubular members is disposed within the other, wherein the first and second tubular elements are axially fixed relative to one another at a fixation location distal to the steerable portion, and wherein the first and second tubular members are axially movable relative to one another along the steerable portion to steer the steerable portion in a first direction, and wherein the first tubular member is adapted to preferentially bend in a first direction.

In some embodiments the second tubular member is substantially uniform and is not adapted to preferentially bend.

In some embodiments the first tubular member comprises at least one slot therein to define a first spine. The second tubular member can also include at least one slot therein to define a second spine.

In some embodiments the first tubular member comprises a braided material.

In some embodiments the first tubular member is disposed within the second elongate tubular member.

In some embodiments the first tubular member is adapted to be moved axially relative to the second tubular member to apply one of a compressive force and a tensile force to the first tubular member and the other of the compressive force and the tensile force to the second tubular member to steer the steerable portion in a first direction.

In some embodiments the second tubular member is adapted to preferentially bend in a second direction, which can be substantially opposite the first direction.

In some embodiments the second elongate tubular element is a floating tubular member.

One aspect of the disclosure is a steerable medical delivery device. The device includes a steerable portion comprising an outer tubular member and an inner tubular member, wherein the inner tubular member is disposed radially within the outer tubular member, wherein the outer tubular member includes at least one outer slot therein to define an outer spine, wherein the inner tubular member includes at least one inner slot therein to define an inner spine, the inner and outer spines being offset relative to one another, and wherein the outer tubular member and the inner tubular member are axially movable relative to one another along the steerable portion and are axially fixed relative to one another at a location distal to the steerable portion.

In some embodiments the outer tubular member comprises a plurality of discontinuous slots to define the outer spine.

In some embodiments the inner tubular member comprises a plurality of discontinuous slots to define the inner spine.

In some embodiments the inner and outer spines are offset substantially 180 degrees from one another.

In some embodiments the inner and outer spines are adapted to receive one of a compressive force and a tensile force to steer the steerable portion of the delivery device. The inner spine can be adapted to receive a compressive force thereto and the outer spine can be adapted to receive a tensile force thereto to steer the steerable portion of the delivery device in a first direction. Alternatively, the inner spine is adapted to receive a tensile force thereto and the inner spine is adapted to receive a compressive force thereto to steer the steerable portion of the delivery device in a first direction.

In some embodiments the inner and outer slots are in substantial alignment relative to a longitudinal axis of the steerable portion when the steerable portion is in a straightened configuration. The inner and outer slots can be substantially perpendicular to the longitudinal axis of the steerable portion when the steerable portion is in a straightened configuration.

In some embodiments the inner and outer slots are not in alignment relative to a longitudinal axis of the steerable portion when the steerable portion is in a straightened configuration.

In some embodiments at least one of the outer slot and the inner slot includes a first interlocking element and a second interlocking element each adapted to allow relative movement therebetween when in a first configuration and each further adapted to prevent movement therebetween when in a second configuration.

In some embodiments the delivery device further comprises a fixation element distal to the steerable portion adapted to prevent axial movement between the outer tubular element and the inner tubular element.

In some embodiments the inner tubular member has an inner surface, and wherein the inner surface is sized to allow a medical device to be advanced therethrough.

One aspect of the disclosure is a method of steering a medical delivery device. The method includes a steerable medical delivery device comprising a steerable portion with an outer tubular member and an inner tubular member, wherein the outer tubular member includes at least one outer slot therein to define an outer spine, and wherein the inner tubular members includes at least one inner slot therein to define an inner spine, the inner and outer spines being offset relative to one another. The method includes applying a compressive force to one of the inner and outer spines and a tensile force to the other of the inner and outer spines to steer the steerable portion from a first configuration to a second configuration. The method also includes preventing relative axial movement of the inner tubular member and outer tubular member at a location distal to the steerable portion while the steerable portion is being steered.

In some embodiments the applying step comprises applying the compressive force to the inner spine, and wherein applying the compressive force to the inner spine causes the tensile force to be applied to the outer spine to steer the steerable portion. Applying the compressive force to inner spine can include moving the inner tubular member distally relative to the outer tubular member.

In some embodiments the applying step comprises applying the tensile force to the inner spine, and wherein applying the tensile force to the inner spine causes the compressive force to be applied to the outer spine to steer the steerable portion. Applying the tensile force to the inner spine can include moving the inner tubular member proximally relative to the outer tubular member.

In some embodiments the applying step comprises applying the compressive force to the outer spine, and wherein applying the compressive force to the outer spine causes the tensile force to be applied to the inner spine to steer the steerable portion. Applying the compressive force to the outer spine can include moving the outer spine distally relative to the inner tubular member.

In some embodiments the applying step comprises applying the tensile force to the outer spine, and wherein applying the tensile force to the outer spine causes the compressive force to be applied to the inner spine to steer the outer spine. Applying the tensile force to the outer spine can include moving the outer tubular element proximally relative to the inner tubular member.

One aspect of the disclosure is a steerable medical delivery device. The medical device includes an elongate member comprising a steerable portion adapted to be steered in a first direction, and a floating element disposed within the steerable portion, wherein the floating element is axially fixed relative to the elongate member at a location proximal to the steerable portion, and is not axially fixed relative to the elongate member along the steerable portion.

In some embodiments the elongate member is a catheter.

In some embodiments the elongate member comprises an inner tubular member with an inner slot therein to define a first spine, and an outer tubular member with an outer slot therein to define an outer spine, wherein the spines are offset from one another.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the disclosure herein. A better understanding of the features and advantages of the present invention will be obtained by reference to the following detailed description that sets forth illustrative embodiments, in which the principles of the disclosure are utilized, and the accompanying drawings of which:

FIG. 8 illustrates an exemplary steerable portion including an outer slotted tubular member and an inner slotted tubular member, with an intermediate tubular element therebetween.

FIG. 9 illustrates an exemplary steerable portion including an outer slotted tubular member and an inner non-slotted tubular member.

FIG. 10 illustrates an exemplary steerable portion including an inner slotted tubular member and outer non-slotted tubular member.

FIG. 11a is a representation of a pattern for use in a steerable portion capable of being cut from a tube or created by winding a ribbon into a tube.

FIG. 11b illustrates a section of a ribbon for use in the tube of FIG. 11a.

FIGS. 12a and 12b are different views of a groove pattern for use in a steerable portion.

FIGS. 16a and 16b illustrate a portion of a tubular member formed with the cut pattern from FIG. 15, while FIG. 16c illustrates compressive and tensile forces acting thereon.

FIG. 17 is a graph illustrating Force v. Displacement behavior associated with the application of loads or displacements at various points around the tubular member shown in FIGS. 15-16c.

FIG. 23 is a flattened view of an exemplary tubular member with more than one spines.

FIG. 24 is a flattened view of an exemplary member with a single substantially straight spine.

FIG. 25 illustrates a flattened portion of an exemplary tubular member. The slots create a relatively neutral pattern.

FIG. 26 illustrates a flattened portion of an exemplary tubular member including interlocking features with complimentary curved surfaces that are adapted to support rotation of the tubular member.

FIGS. 30A-30H illustrate exemplary beads that can be used in a lockable guiding device.

DETAILED DESCRIPTION OF THE INVENTION

The disclosure relates generally to steerable delivery devices, which may be considered steerable guide devices, and their methods of use. The steerable delivery devices can be used to deliver, or guide, any type of suitable medical device or instrument therethrough to a location within a patient's body. For example, the steerable delivery devices can be used to deliver, or guide, a medical device into bodily lumens such as, for example without limitation, a blood vessel, an esophagus, a trachea and possibly adjoining bronchia, any portion of the gastrointestinal tract, an abdominal cavity, a thoracic cavity, various other ducts within the body, and the lymphatics. Once the steerable delivery device has gained access to a target location within the subject, the medical device or instrument is delivered, or guided, to the target location to carry out the medical intervention. Steerable delivery devices described herein can be tracked along a previously delivered guide wire.

Figure 1:
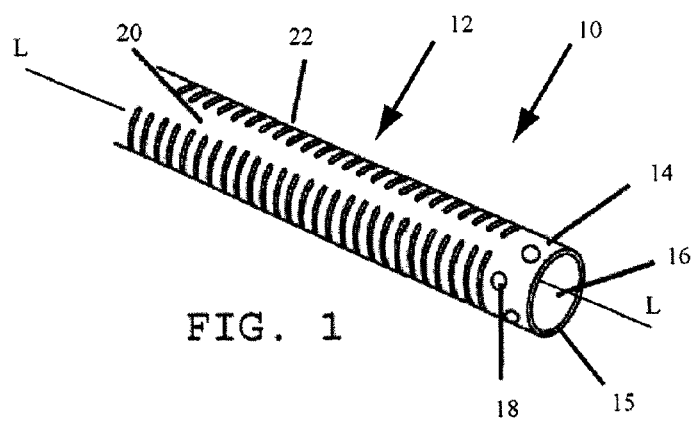
FIG. 1 is a perspective view of a steerable portion of a steerable medical delivery device.

FIG. 1 is a perspective view of a distal portion of an exemplary steerable delivery device. Steerable device 10 includes steerable portion 12 and has distal end 15. Steerable portion 12 includes an outer tubular member 14 and inner tubular member 16. Outer tubular member 14 has an inner surface defining a lumen therein, and inner tubular member is sized to be disposed within the inner lumen of outer tubular member 14. Outer tubular member 14 and inner tubular member 16 are axially fixed relative to one another at fixation location 18 along the length of steerable device 10. That is, at fixation location 18, the inner and outer tubular members are not adapted to move distally or proximally relative to one another. Fixation location 18 is located distal to steerable portion 12. At locations proximal to fixation location 18, inner tubular member 16 and outer tubular member 14 are axially movable relative to one another. That is, along steerable portion 12, inner tubular member 16 and outer tubular member 14 are adapted to move axially relative to one another. Outer tubular member 14 has slots 22 formed therein to define spine 20. Spine 20 extends along a length of steerable portion 12. Slots 22 are shown substantially perpendicular to the longitudinal axis "L" of steerable portion 12, when steerable portion 12 is in a straightened configuration as shown in FIG. 1. Inner tubular member 16 also has slots formed therein (not shown) in the steerable portion to define a spine (not shown).

Figure 2A:
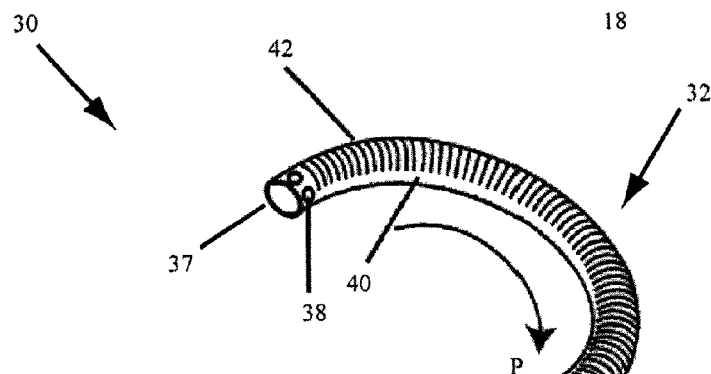
FIGS. 2a, 2b, and 2c illustrate steering of exemplary steerable portions of steerable medical delivery devices
Figure 2B:
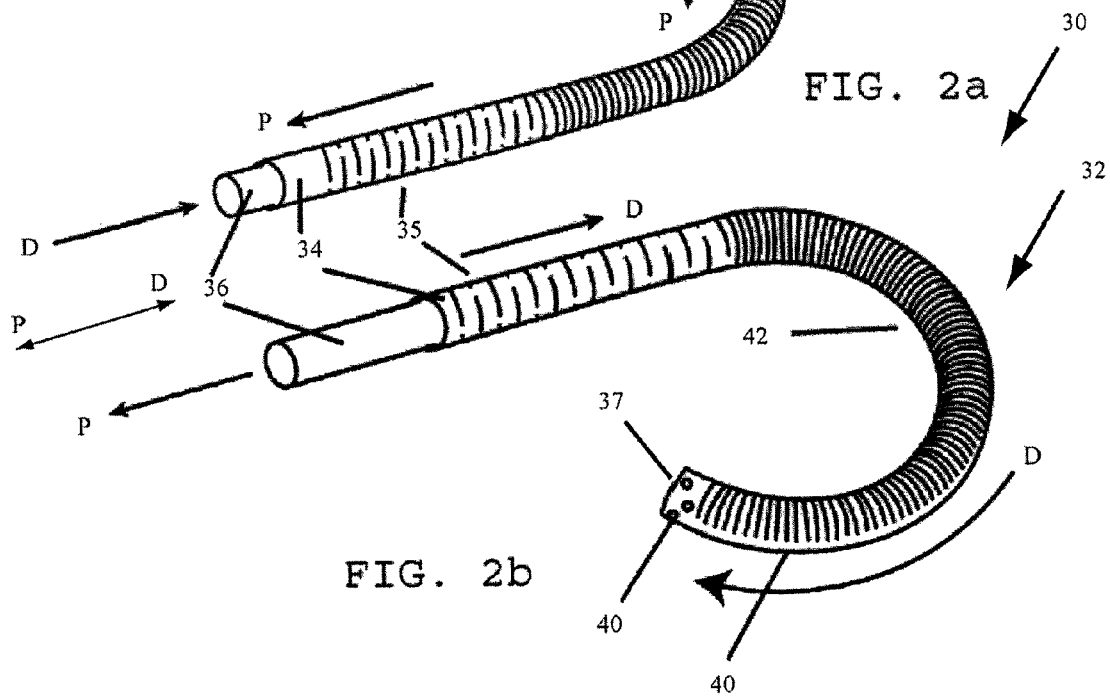

FIGS. 2a and 2b illustrate an exemplary embodiment of a steerable delivery device. Steerable device 30 has a distal end 37 and includes outer tubular element 34 and inner tubular element 36 which are axially immovable relative to one another at fixation location 38, but are axially movable proximal to fixation location 38. Outer tubular element 34 includes a plurality of slots 42 formed therein to define spine 40. Inner tubular element 36 also includes a plurality of slots formed therein (not shown) to define a spine (not shown). In FIGS. 2a and 2b, the spines are disposed substantially 180 degrees apart from one another. FIG. 2a illustrates steerable portion 32 deflected, or steered, into a first bent configuration, while FIG. 2b illustrates steerable portion 32 steered into a second bent configuration different than the first bent configuration. To steer the steerable portion into the configuration shown in FIG. 2a, a proximal portion of outer tubular member 34 is moved axially, and specifically proximally, relative to inner tubular member 36, while the tubular elements 34 and 36 are axially fixed relative to one another at fixation location 38. This can be accomplished by pulling outer tubular member 23 in a proximal "P" direction while maintaining the position of inner tubular member 36, by pushing inner tubular member 36 in a distal "D" direction while maintaining the position of outer tubular member, or by a combination thereof. The relative axial movement of the inner and outer tubular members as shown in FIG. 2a applies substantially opposing compressive and tensile forces to the spines of the tubular members, thus deflecting, or steering, the device in the direction of spine 40 of outer tubular member 34, as is shown in FIG. 2a. FIG. 2b illustrates a step of steering device 30 in the substantially opposite direction from that shown in FIG. 2a. To steer device 30 into the configuration shown in FIG. 2b, inner tubular member is moved proximally relative to outer tubular member 34. This can be performed by moving the outer tubular member distally, moving the inner tubular member proximally, or a combination thereof. This relative axial movement applies substantially opposing compressive and tensile forces to the spines in steerable portion 32 of device 30, thereby deflecting the device in a direction substantially opposite that of spine 40 of outer tubular member 34.

Figure 2C:
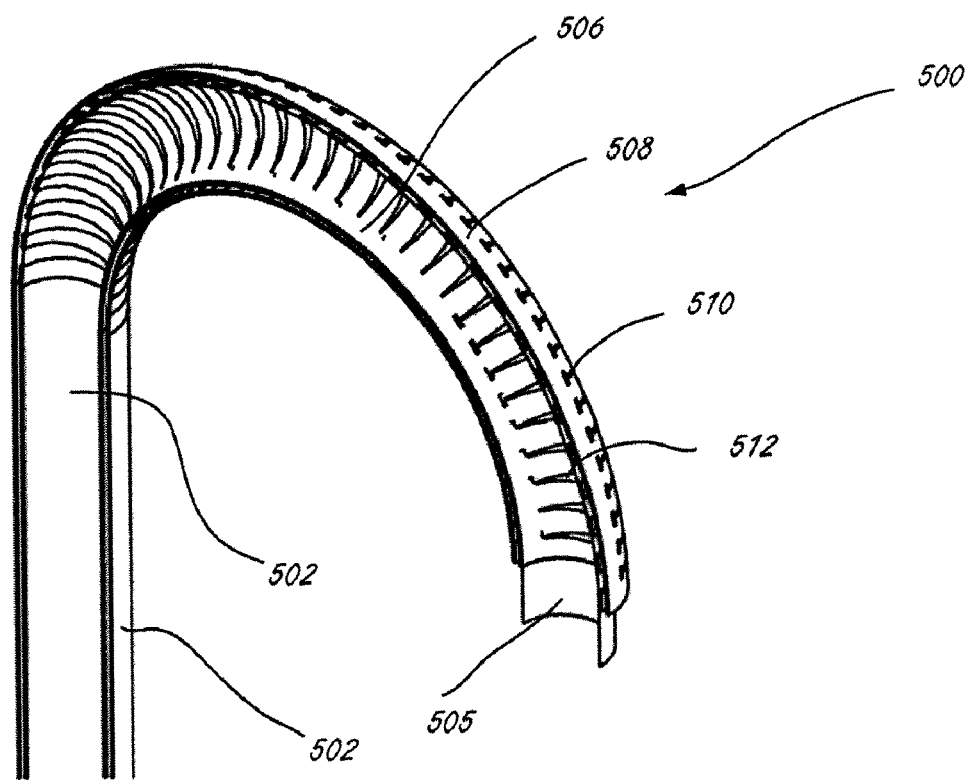

FIG. 2c shows a sectional view of the steerable portion from FIG. 2b, including optional floating tubular member 505 disposed within inner tubular member 504. Steerable portion 500 includes inner tubular member 504 and outer tubular member 502. Inner tubular member 504 has interrupted slots 512 formed therein to define spine 506. Outer tubular member 502 has interrupted slots 510 formed therein to define spine 508. The steerable portion is bent along the axis of spine 506. Spine 508 and spine 506 are substantially 180 degrees apart from one another (i.e., they are on substantially opposite sides of steerable portion 500).

To steer steerable portion 500 into the configuration shown in FIG. 2c (also shown in FIG. 2b), inner tubular member 504 is pulled in the proximal direction relative to outer tubular member 502, as is illustrated in FIG. 2b. Pulling on the inner member 504 applies a tensile force to inner spine 506. Because inner and outer tubular members 504 and 502 are axially fixed relative to one another at a location distal to the steerable portion, pulling on inner member 504 relative to outer tubular member 502 results in a compressive force applied to the distal end of the steerable portion of outer tubular member 502. The compressive force begins to compress slots 510 on outer tubular member 502. Compression of outer slots 510 causes outer tubular member to bend in the direction shown in FIG. 2c, and the bending stops when inner slots 510 are closed. Thus, outer slots 510 limit the degree of the bend of steerable portion 500. The same type of bending that is shown in FIGS. 2b and 2c would occur if outer tubular element 502 were pushed distally relative to inner tubular member 504.

If outer tubular member 502 were pulled proximally relative to inner tubular member 504 (or if inner tubular member 504 were pushed distally relative to outer tubular member 502), steerable portion 500 would bend in the manner shown in FIG. 2a. The degree of the bend would be limited by inner slots 512.

FIG. 2c illustrates an embodiment of a medical device including a floating tubular member, which may be referred to herein as a floating liner. In general, a floating liner is disposed within an outer structure. In the exemplary embodiment in FIG. 2c, the outer structure includes the inner and outer tubular members. The outer structure generally provides structural and mechanical properties for the delivery device, and the floating liner provides lubricity for a medical device or instrument to be advanced therethrough. A floating liner is generally impermeable as well. A floating liner "floats" with a portion of the outer structure. That is, the floating liner is not fixed to a portion of the outer structure in which it floats. In the exemplary embodiment in FIG. 2c, the floating liner floats within the steerable portion (i.e., is not attached to the steerable portion). In general, a floating liner is attached to the outer structure at a location proximal to the steerable or bendable portion of the device. For example, in the embodiment in FIG. 2C, the floating liner is attached to the outer structure at a location proximal to the steerable portion. A floating liner doesn't impede the ability of the outer structure to move as it is steered, bent, actuated, receives forces applied thereto, etc.

In some embodiments the floating liner is a lubricious polymer tube. In some embodiments the floating liner includes wire windings and/or axially laid wires.

The outer structure in which the floating liner floats can be any suitable tubular member. For example, the outer structure can be a catheter, guiding device, a steerable device, etc. In some embodiments the outer structure has a neutral bending preference but is not intended to be steered. In this embodiment the outer structure provides axial and radial stiffness thereby limiting the likelihood of kinks while the floating liner provides lubricity and is additionally restrained from kinking by the outer structure.

FIGS. 2a and 2b also show proximal portion 35 of device 30, which is proximal to steerable portion 32, having a substantially neutral portion designed to have no preferential bending axis while at the same time transmitting axial force and torque applied at a proximal end of the device (not shown).

In some embodiments, the inner and outer tubular members are adapted to have opposing compressive and tensile loads applied thereto to steer the steerable portion. In some embodiments at least one of the tubular members has a neutral bending axis. A neutral bending axis, as used herein, generally refers to an axis of the tubular member along which there is substantially no axial displacement in response to a compressive and/or tensile force applied thereto. Axial displacement along the neutral bending axis, in response to a compressive and/or tensile force applied thereto, is less than axial displacement of structures elsewhere in the tubular member. In particular, axial displacement along the neutral bending axis is minimal relative to axial displacement of structures elsewhere in the tubular member. Examples of a neutral bending axis include spine 382 in FIG. 21 and spines 412 and 414 in FIG. 23.

In some embodiments at least one of the tubular members is adapted to offset the neutral bending axis relative to the opposite tubular member. The neutral bending axes of the tubular members can be offset to be approximately tangent to opposite sides of the opposing members, making the neutral bending axis offset equal to the diameter of the device, thus providing the highest possible bending leverage ratio for a given device diameter.

The tubular members described herein may exhibit preferential or neutral bending behavior. Neutral bending behavior implies that the displacement for a given radially applied load (from the edge of the tubular member through the longitudinal axis of the tubular member) will be independent of the radial angle from which the load was applied. In contrast, in a non-neutral structure the displacement associated with a radial load will change as a function of the radial angle. An exemplary tubular member tending towards neutral bending behavior is shown in FIG. 25 or the uninterrupted spiral pattern of FIG. 25 which is essentially a spring.

In some embodiments the inner and outer tubular elements are adapted to be rotated relative to one another to enhance the steerability of the steerable portion. The tubular elements can rotate relative to one another yet remain axially fixed relative to one another at a location distal to the steerable portion. In these embodiments, in addition to axial forces being applied to one or more tubes, one or more tubular members are also rotated with respect to each other to steer the steerable portion.

In some embodiments only one of the inner and outer tubular members has at least one slot defining a spine along the steerable portion, while the other does not have any slots along the steerable portion. For example, in FIGS. 2a and 2b, outer tubular member 34 can have a slot and a spine while inner tubular member 36 does not have a slot formed therein. Alternatively, inner tubular member 36 can have at least one slot and a spine while outer tubular member 34 does not have a slot formed therein. The steerable portion can be steered as described herein if at least one of the inner and outer tubular members is adapted to preferentially bend in a first direction.

In the embodiment in FIGS. 1 and 2 the slots in both tubular members are substantially perpendicular to the longitudinal axis of the steerable portion. The slots in one or both of the tubular members can be, however, at an angle relative to the longitudinal axis that is other than substantially 90 degrees.

In some embodiments the steerable device also includes a tubular element disposed between the inner and outer tubular members. The intermediate member can be, for example without limitation, a flexible polymeric material. The intermediate member can be encasing one or both of the tubular members, or comprising one or both of the members. The intermediate member can be adapted to provide a fluid barrier and/or a low friction surface.

Slots as described herein can be formed in a tubular member by laser machining or other machining processes. Forming the slots creates at least one spine in a tubular member. A spine as used herein can be considered a region of the steerable portion that imparts axial stiffness in compression or tension, or both, and may additionally include features that provide torsional stiffness. When a single spine is created in a tubular member, the neutral bending axis of the tubular member is moved to the spine of the tubular member.

In some embodiments, a tubular member includes at least two spines, the combination of which moves the neutral bending axis of the tubular member to an axis parallel to, or tangent to when bent, the longitudinal axis of the tubular device and passing through the spines.

In some embodiments a liner, such as a flexible polymer liner, is bonded on the inner surface of the inner tubular member. In some embodiments a flexible polymer is bonded or otherwise disposed over the outer surface of the outer tubular member. A liner can also be disposed such that it is encasing the inner tubular member.

In some embodiments the steerable portion is comprised of a first tubular member that is adapted to bend preferentially in a first direction and a second tubular member that is not adapted to bend preferentially in one direction. In some instances of these embodiments, the second tubular member is a flexible polymer material with or without a braided or wire support. In some instances, a wire or other structural support is included in the first tubular member in the deflectable area to increase compressive and tensile stiffness along one side of the tubular member, thus moving the neutral bending axis from the longitudinal axis of the tubular member to the side of the tubular member that includes the structural support. In some instances wires are laid longitudinally and distributed evenly to increase axial stiffness in tension without creating a preferential bending.

In some embodiments the device includes three tubular members, having three offset neutral bending axes approximately 120 degrees radially spaced apart, thus providing the steerable device with universal steering in any direction.

Figure 3:
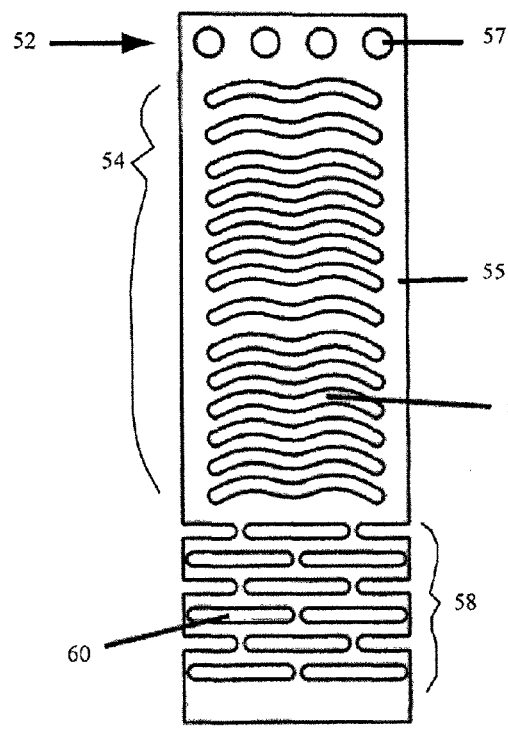
FIG. 3 illustrates a flattened view showing an exemplary slot pattern for use in a steerable portion of a delivery device.

FIG. 3 illustrates, for ease of description, a flattened, or unrolled, portion of exemplary tubular member 50, which can be an inner or an outer tubular member. Tubular member 50 includes fixation region 52, steerable portion 54, and a proximal neutral portion 58. Steerable portion 54 includes a plurality of slots 56 formed therein to define spine 55 extending along the steerable portion. Slots 56 are sinuous-shaped slots, and spine 55 has a generally straight configuration along the length of steerable portion 54. That is, spine 55 is substantially parallel with the longitudinal axis of the tubular member. Fixation region 52 includes a plurality of holes 57 to facilitate bonding to provide for axial fixation relative to a second tubular member (not shown). Proximal portion 58 includes a plurality of multiple overlapping slots 60 to provide the desired flexibility, axial force transmission, and torque transmission characteristics.

Figure 4:
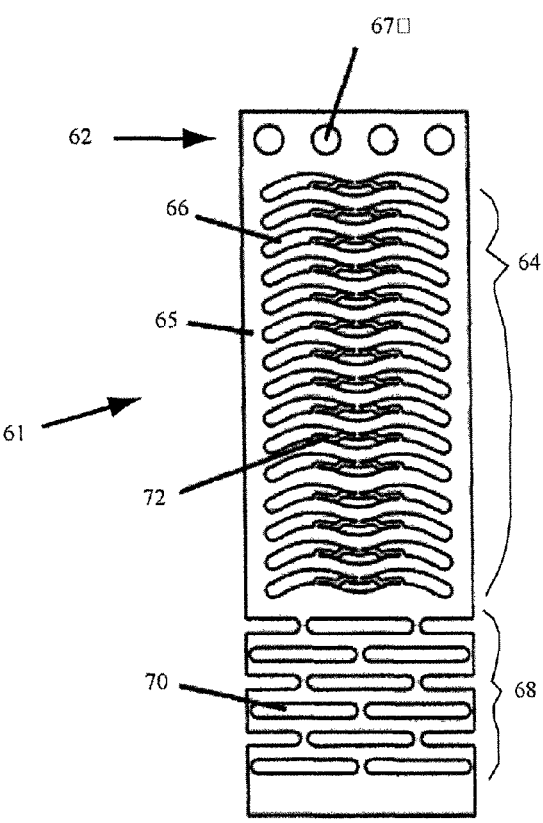
FIG. 4 illustrates a flattened view showing an exemplary slot pattern for use in a steerable portion of a delivery device.

FIG. 4 illustrates a flattened, or unrolled, portion of exemplary tubular member 61, which can be an inner or an outer tubular member of a steerable portion. Tubular member 61 includes fixation region 62, steerable portion 64, and proximal neutral bending portion 68. Neutral bending portion 68 will exhibit minimal bending preference upon a compressive or tensile force applied thereto. Tubular member 61 is similar to tubular member 50 shown in FIG. 3, but includes linking elements 72, which can be flexible. Each linking element extends from one side of a slot to the other side. Each linking element includes two arm portions extending from one side of the slot to the other side of the slot. The two arms meet at the point at which they are connected to one side of the slot. The linking elements extend along steerable portion 64 on substantially the opposite side as spine 65. Linking elements 72 enhance and/or control torque response and bending of steerable portion 64. As steerable portion 64 is bent about spine 65, linking elements 72 bend and stretch under tension. As steerable portion 64 is twisted, or put in torque, linking elements 72 are put in compression. In torque, the gap between a given linking element and the section of the tubular member proximally adjacent to the given linking element collapses, effectively increasing the torsional stiffness of steerable portion 64.

Figure 5:
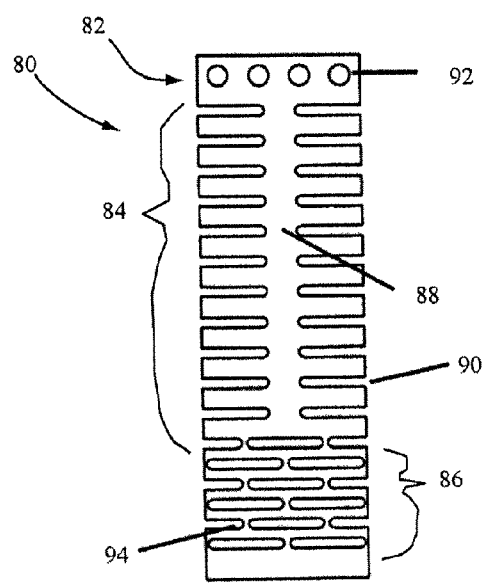
FIG. 5 illustrates a flattened view showing an exemplary slot pattern for use in a steerable portion of a delivery device.

FIG. 5 illustrates a flattened portion of exemplary tubular member 80, including fixation portion 82, steerable portion 84, and proximal neutral portion 86. The embodiment in FIG. 5 is similar to the outer tubular member as shown in FIGS. 2a and 2b. Steerable portion 84 includes substantially straight slots 90 that are substantially perpendicular to the longitudinal axis of tubular member 80. Spine 88 is substantially straight in configuration, extending along the length of steerable portion 84 substantially parallel to the longitudinal axis of the tubular member 80. Fixation portion 82 includes holes 92 therethrough (four shown) to facilitate bonding. Proximal portion 86 has multiple overlapping slots 94 to give the desired flexibility, axial force and torque transmission.

Figure 6:
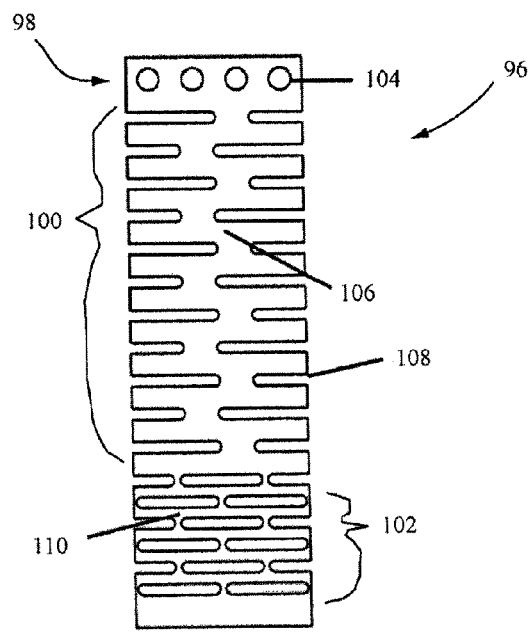
FIG. 6 illustrates a flattened view showing an exemplary slot pattern for use in a steerable portion of a delivery device.

FIG. 6 illustrates a flattened portion of exemplary tubular member 96, including fixation portion 98, steerable portion 100, and proximal neutral portion 102. Steerable portion 100 includes substantially straight slots 108 that are substantially perpendicular to the longitudinal axis of tubular member 96, but each is offset relative to the adjacent slot so that spine 106 has a sinuous shape extending along the length of steerable portion 100. Fixation portion 98 includes holes 104 therethrough (four shown) to facilitate bonding. Proximal portion 102 includes multiple overlapping slots 110 to give the desired flexibility, axial force and torque transmission characteristics.

Figure 7A:
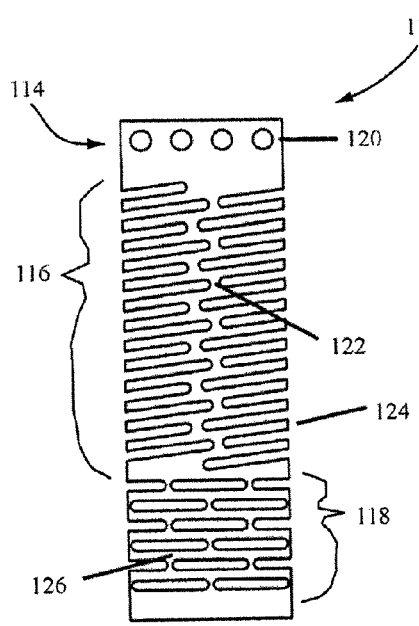
FIGS. 7a and 7b illustrate flattened views showing exemplary slot patterns for use in a steerable portion of a delivery device.
Figure 7B:
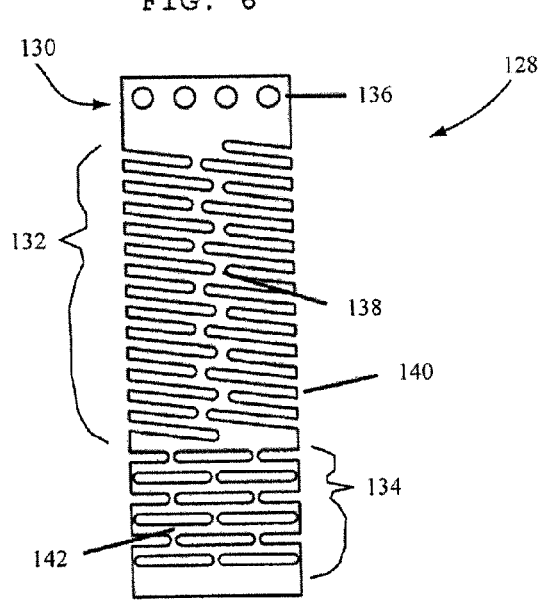

FIGS. 7a and 7b illustrate exemplary portions of flattened first and second tubular members 112 and 128. First tubular member 112 can be an inner tubular member and second tubular member 128 can be an outer tubular member, or first tubular member 112 can be an outer tubular member and second tubular member 128 can be an inner tubular member. Tubular members 112 and 128 can be assembled as part of a steerable delivery device. That is, one of the first and second tubular members can be disposed within the other. First tubular member 112 includes fixation portion 114, steerable portion 116, and proximal neutral portion 118. Fixation portion 114 includes holes 120. Steerable portion 116 has slots 124 formed therein to define spine 122. Spine 122 has a generally sinuous shape. Proximal portion 118 includes a plurality of overlapping slots 126. Second tubular member 128 includes fixation portion 130, steerable portion 132, and proximal neutral portion 134. Fixation portion 130 includes holes 136. Steerable portion 132 has slots 140 formed therein to define spine 138. Spine 138 has a generally sinuous shape. Proximal portion 134 includes a plurality of overlapping slots 142.

In FIGS. 7a and 7b, the slots in each of tubular members 112 and 128 are offset relative to the adjacent slot, interrupted, and have a general helical configuration. Spines 122 and 138 have generally sinuous configurations. The slots in the tubular members are at the same angle relative to the longitudinal axis of the tubular member, but are formed in opposite helical patterns. A advantage of having inner and outer tubular members with slots that are not in alignment (as opposed to inner and outer tubular members that have slots perpendicular to the longitudinal axis of the tubular member)

is that the slots are less likely to get caught up on one another as the steerable portion is steered. The angled slots shown in FIGS. 7a and 7b also provide for an increased torque response based on a torque applied at the proximal end of the device.

FIG. 8 illustrates a portion of an exemplary steerable delivery device. Steerable device 150 includes outer tubular member 152, inner tubular member 154, and intermediate tubular member 156. A portion of outer tubular member 152 and intermediate member 156 are cut away to show inner tubular member 154. Intermediate tubular member 156 can be a flexible polymeric tube. Inner and outer tubes 152 and 154 have slots 160, 164 formed therein to define spines 158 and 162. The spines are substantially 180 degrees apart, as shown. The slots formed in the respective tubular members are at an angle relative to the longitudinal axis of the steerable portion and are formed in opposite helical patterns.

FIG. 9 illustrates a portion of an exemplary steerable delivery device. Steerable device 166 includes outer tubular member 168 and inner tubular member 170. Inner tubular member 170 can be a flexible polymeric tubular element. Outer tubular member 168 has a plurality of slots 174 formed therein to define spine 172. Inner tubular member 170 has no preferential bending axis. Inner tubular member 170 could alternatively have a modified bending axis offset by having, for example, a stiffening element incorporated into the wall of inner tubular member 170 approximately 180 degrees from spine 172. In some embodiments inner tubular member 170 may incorporate wire braids and or axially-laid wires which reduce kinkability and increase axial stiffness as is common in braided catheters or other similar known tubular medical devices.

FIG. 10 illustrates a portion of an exemplary steerable delivery device. Steerable delivery device 178 includes outer tubular member 180 and inner tubular member 182. Outer tubular member 180 can be, for example, a flexible polymeric tubular member. Inner tubular member 182 has a plurality of slots 186 formed therein to define spine 184, which is substantially parallel to the longitudinal axis of the steerable portion. Outer tubular member 180 has no preferential bending axis. Alternatively, outer tubular member 180 can have a preferential bending axis. For example, a structural support element can be incorporated into the wall of outer tubular member 180 approximately 180 degrees from spine 184. Outer tubular member 180 can be substantially the same as inner tubular element 170 in FIG. 9, but for any lubricity enhancing feature. In some embodiments inner tubular member 170 may incorporate wire braids and or axially laid wires which reduce kinkability and increase axial stiffness as is common in braided catheter or other similar known tubular medical device.

In an alternative embodiment, the device includes inner and outer slotted tubes, and additionally includes an outermost tubular member similar to 180 shown in FIG. 10. The outermost tubular member can be, for example without limitation, a polymeric tubular member.

FIG. 11a illustrates a portion of an exemplary embodiment of a first tubular member that can be included in a steerable delivery device. Tubular member 190 is a tubular member formed from a ribbon wire. Tubular member 190 has spine 192 formed by coiling a ribbon shaped with interlocking elements 194 and 196, which together form an interlocking feature along spine 192. Interlocking elements 194 and 196 may be press-fit to interlock the two. The interlocking elements can be encased with a tubular member, such as a polymer tubular member, to secure them in place. The interlocking elements can also, or alternatively, have a polymer tubular member disposed therein to help secure them in place.

In addition to the interlocking features, the ribbon wire has sections of decreased width 198 which once wound into a tubular structure create the steerable portion for flexibility. A second tubular member of the steerable delivery device can be created in a similar manner to the tubular member in FIG. 11a. FIG. 11b illustrates an embodiment of the ribbon with interlocking elements 196 and decreased width regions 200 between elements 196. The angle of interlocking elements 196 relative to the longitudinal axis of the tubular element can be varied based on the pitch of the coil. Such a pattern can additionally be fabricated by laser machining.

FIGS. 12a and 12b illustrate an exemplary embodiment of a tubular member. Tubular member 210 comprises a tube 214 with grooves 212 formed therein on the outer surface of tube 214. Grooves 212 do not extend all the way through tube 214. Tubular member can be, for example, a stiff polymeric tubular member. FIG. 12a shows a sectional view of a portion of tubular 210 showing the depth of grooves 212 in the steerable portion. FIG. 12b illustrates a flattened view of tubular member 210 showing grooves 212 formed in tube 214. Grooves 212 define a single substantially straight spine 216. Grooves 212 cut into tube 214 increase flexibility of the steerable portion to allow the steerable portion to be steered. Spine 216 provides for the application of compressive and tensile forces to steer the device. Because the cut does not go all the way through the wall of the tube, it inherently creates a fluid tight barrier and a lubricious liner. In some embodiments tubular member 210 can an inner or outer tubular member of a steerable device, and the other of the inner and outer tubular elements can also includes a tubular element with grooves formed thereon. In some embodiments the steerable device can also have a polymeric sleeve to encapsulate the outer tube to create a smooth outer surface.

Figure 13A:
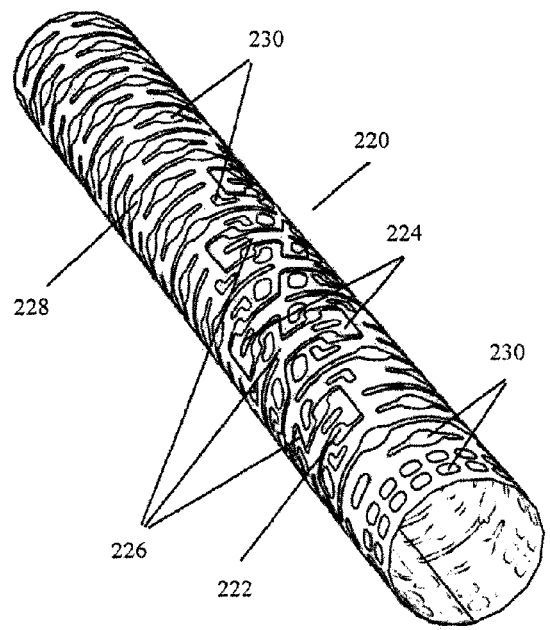
FIGS. 13a, 13b, and 13c are various views of a cut pattern for use in a guide catheter
Figure 13B:
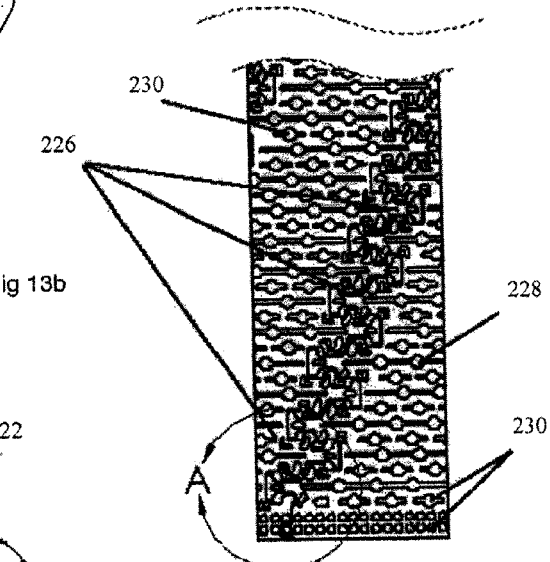
Figure 13C:
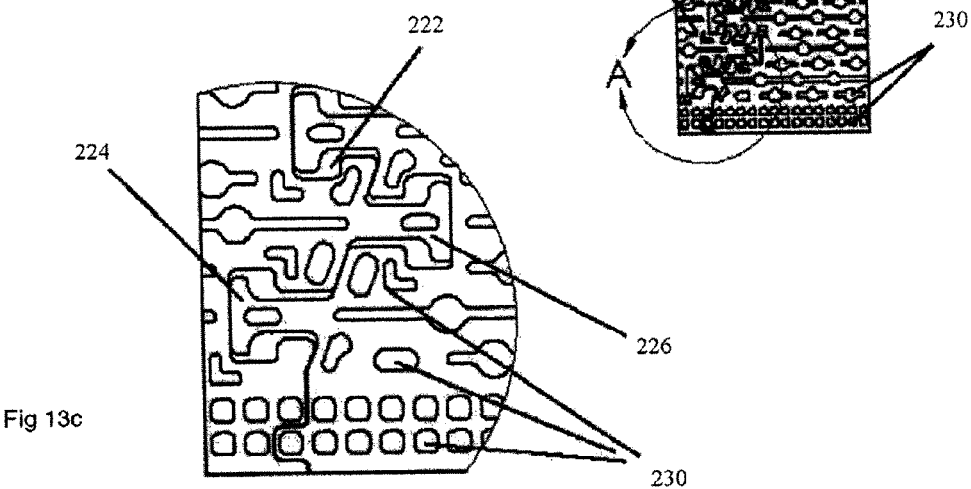

FIG. 13a illustrates a portion of an exemplary introducer sheath reinforcement member 220. Member 220 is formed by laser cutting a tubular member to slots or gaps therein. A helical slot 222 defines interlocking T-shaped patterns 224 formed in reinforcement member 220. The helical path is shown generally in helical path 226. Flexibility slots 228 are formed in member 220 to provide flexibility to member 220. Member 220 also includes bonding slots 230 formed therein to allow for bonding to one or more components of the device. FIG. 13b illustrates member 220 from FIG. 13a in a flattened pattern showing the interlocking T-shaped pattern along helical path 226, flexibility slots 228, and bonding slots 230. FIG. 13c shows a close-up of the section shown in FIG. 13b.

In some embodiments a guide catheter includes a relatively rigid metal or polymer reinforcement member (an example of which is shown in FIG. 13a-13c) layered between an inner and an outer flexible polymer tube. The rigid reinforcement member can be laser machined or otherwise cut in a pattern in order to enhance flexibility along the longitudinal axis of the tube, to allow some limited radial compliance, and to allow bonding of the inner and outer flexible polymers. The slot pattern can include an interlocking T-shaped pattern arranged helically around the tube for flexibility and radial compliance, a slot pattern where the slots are substantially perpendicular to the tube longitudinal axis, and are patterned along the tube longitudinal axis to further enhance flexibility and bonding of said layers.

Figure 14:
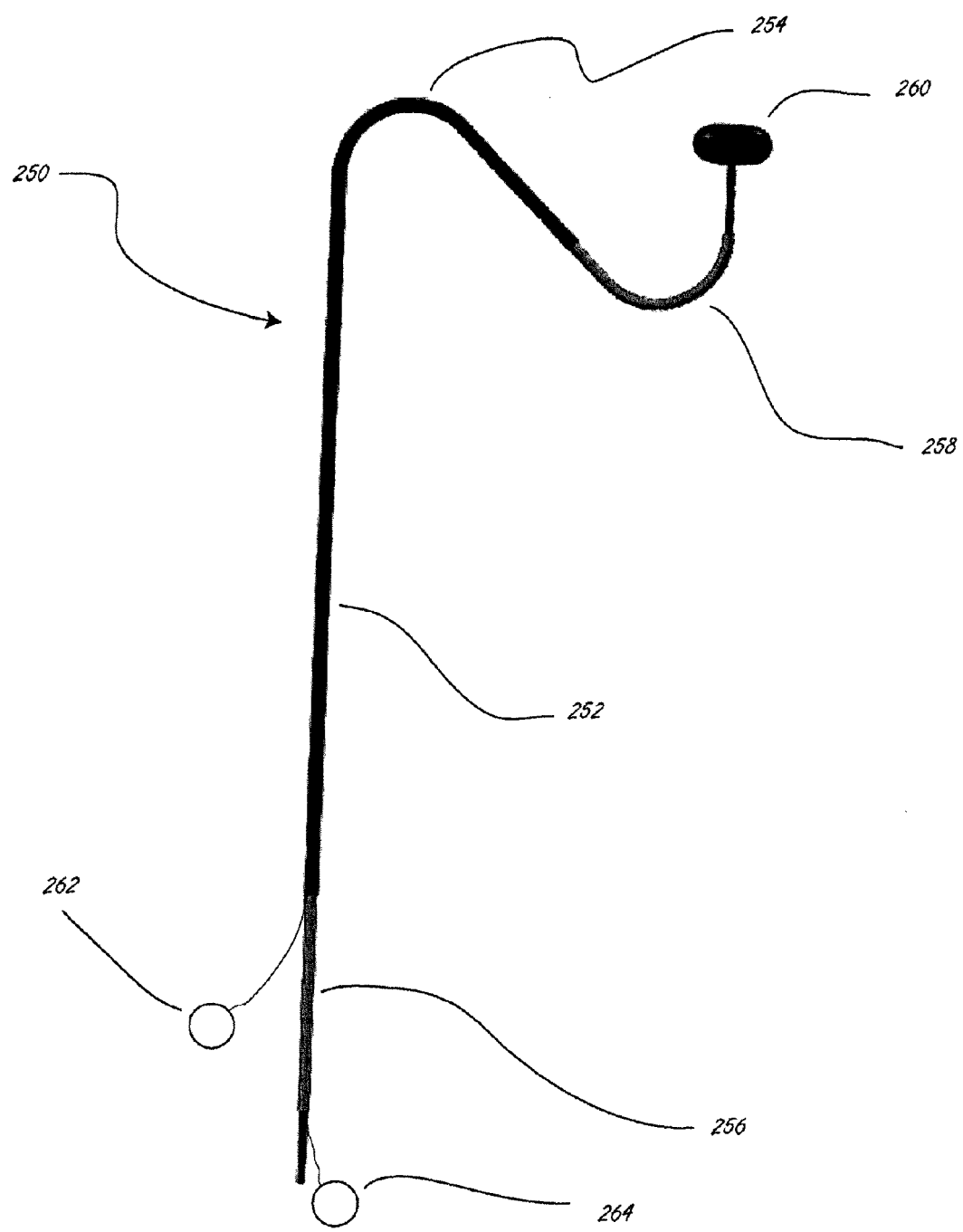
FIG. 14 illustrates an outer guide member and a delivery device therein.

FIG. 14 illustrates an exemplary embodiment of a guide system adapted to guide and deliver a therapeutic, diagnostic, interventional, or any other type of medical device 260 intraluminaly to a target location within a body. Guide system 250 includes outer guide member 252 and steerable delivery device 256, a portion of which is disposed within outer guide member 250. Steerable delivery device 256 can be, for example, any of the steerable delivery devices described herein. Outer guide member 252 has a preset bend 254 that can be formed by, for example, heat setting. Steerable delivery device 256 includes steerable portion 258, which can be formed as, for example, any of the steerable portions described herein. For example, steerable delivery device can include outer and inner tubular members, wherein at least one of the tubular members is adapted to preferentially bend in a first direction. In the embodiment shown in FIG. 14, steerable portion 258 is comprised of a single steerable tubular member steered into the configuration shown in FIG. 14 by actuating pull wire 264. Alternatively, steerable delivery device 256 can be comprised of the embodiment described in FIG. 2, and steered by relative axial movement of inner and outer tubular members, as described herein.

Alternatively, outer guide member 252 can be adapted to be bent using optional pull wire 262, shown in FIG. 14. In such an embodiment bend 254 may or may not preset. Guide member 250 comprises a tubular member incorporating a pattern of slots as described for steering portions herein. When located in position pull wire 262 is tensioned and the axial and torsional stiffness of bend 254 is thereby increased. A steerable outer guide member 252 in its delivery configuration (non-bent) is generally loose and compliant, but is tensioned or compressed to reconfigure it into a pre-set shape. Its stiffness in the bent configuration is a function of the amount of tension or compression applied and the particular slot pattern chosen.

Bend 254 in outer guide member 252 is compliant enough to be straightened for delivery, for example advanced on a guide wire, but rigid enough to be able to guide steerable delivery device 256 around bend 254. Steerable delivery device 256 is steerable and transmits torque.

The structural properties of the inner and outer tubular members of the steerable delivery device will determine the manner in which they respond to force applied thereon. The structural properties of the inner and/or outer tubes will depend on the tubing material and the design, or characteristics, of the slots created in the tubular members (unless one of the inner and outer tubular members does not have any slots therein). The design of the slot pattern is therefore a function of the required structural properties of the tubular member. For example, structural properties of the tubular member that can be modified by changing the design of the slots or slot patterns include flexural stiffness, torque transmission, steerability, radius of curvature, and allowable wall thickness of the steerable assembly.

Figure 15:
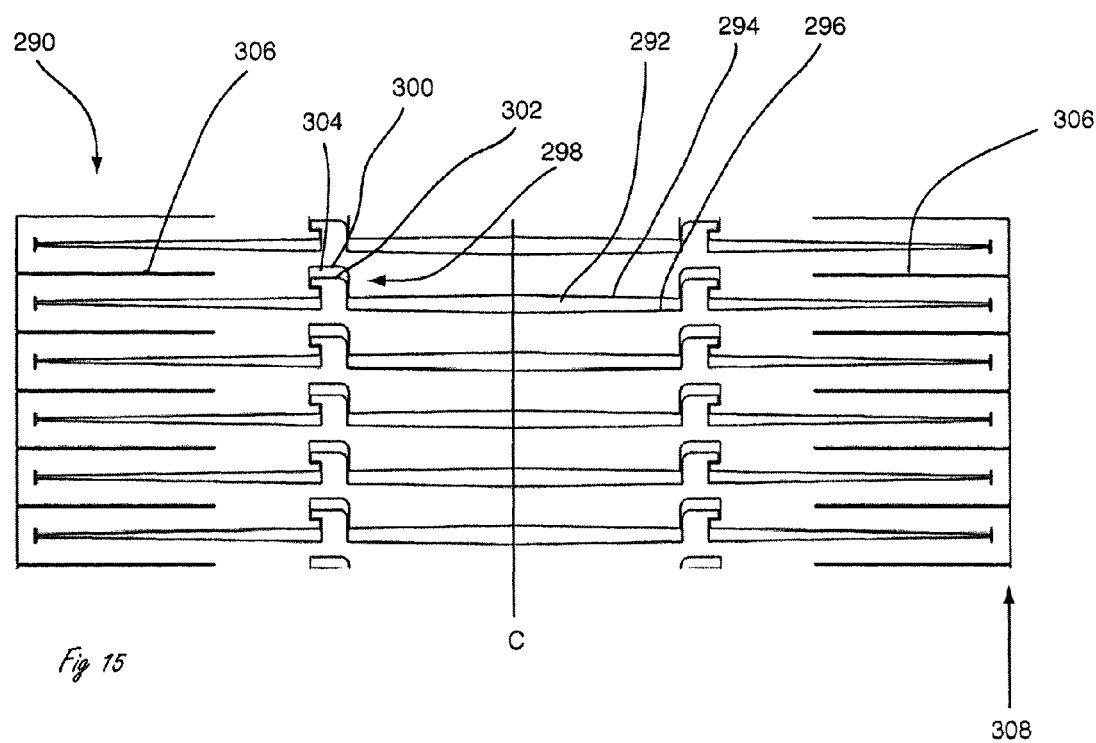
FIG. 15 illustrates a discontinuous cut pattern for use on a tubular member that is most steerable in compression.

FIG. 15 is a flattened view and illustrates a portion of an exemplary steerable portion of a tubular member. Tubular member 290 can be an inner or an outer tubular member as described herein. Steerable portion 290 is typically a laser-cut tubular member, but may in fact be fabricated by any technique capable of creating the appropriate widths of cuts required (e.g., water jet, wire EDM, etc.) wherein first cut, or slot, 292 is made, defined by first surface 294 and second surface 296. Slot 292 extends almost all the way around tubular member 290, and defines spine 308. Slots 292 are thickest, along the tubular longitudinal axis, along compression axis C which allows tubular member 290 to be compressed along compression axis C, which changes the configuration of tubular member 290. Tubular member 290 also includes interlocking features 298 (only one of which is labeled), which include first interlocking element 300 and second interlocking element 302. Slot 292 includes slot portion 304, which is defined by the first and second interlocking elements 300 and 302 and allows for movement between the two interlocking elements 300 and 302 in the axial direction. Tubular member 290 also includes stress relief slots 306, which extend across spine 308 and provide stress relief for spine 308. Stress relief slots 306 can be considered to be axially in-between slots 292. Slots 292 are not connected with slots 306. Slots 306 are substantially thinner than slots 292. As will be described in detail below, tubular member 290 is adapted to be compressed along compression axis C, which is substantially 180 degree from spine 308.

FIGS. 16a and 16b illustrate a portion of tubular member 290 shown in FIG. 15. FIG. 16b illustrates tubular member 290 with slot 292, with a greatest thickness along compression axis C. Slot 292 includes slot 304, which is defined by interlocking elements 300 and 302. Slot 292 and slot 304 allow for compression of tubular member 290, shown in FIG. 16a. When a compressive force A is applied along compressive axis C surfaces 294 and 296 are brought closer towards another, as are surfaces 300 and 302. Slots 292 and 304 therefore allow for axial compression of tubular member 290, until surfaces 294 and 296 engage one another, or until surfaces 300 and 302 engage one another, whichever happens first. Slots 292 and 304 can be designed such that the slots close at the same time. Once the surfaces engage, they behave substantially like a solid tube and can no longer be compressed along the engagement points. Upon a compressive force to tubular member 290, tubular member will therefore be steered into the configuration shown in FIG. 16a. Similarly, when a tensile force is applied to tubular member 290 shown in FIG. 16a, tubular member 290 will straighten to the configuration shown in FIG. 16b. Particularly, tubular member 290 will straighten until the interlocking features engage one another and prevent further movement. FIG. 16c illustrates the tubular member from FIGS. 16a and 16b and indicates points of load application including those illustrated in FIGS. 16b and 16c. Torsional force T indicates a torsional force acting on tubular member 290 upon the application of torque at a proximal end of the device. Tensile and compressive forces are listed as "a" or "b" depending on the behavior exhibited by the tubular member as described below.

FIG. 17 is a graph illustrating Force v. Displacement behavior associated with the application of loads or displacements at various points around tubular member 290 shown in FIGS. 15-16c. The Force/Displacement behavior of tubular member 290 for loads applied in planes passing through the longitudinal axis of the tubular member, ranges between the lines A and B in FIG. 17. Curve A illustrates the behavior along a compliant axis on the surface of the tubular member and parallel to the longitudinal axis of the tubular member where the slots are widest, while curve B illustrates the behavior where the slots are vary narrow. As the tubular member is bent about spine 308 in a fashion which closes slots 292, the forces required to bend the tubular member are low and the Force/Displacement curve has a small slope. The tubular member is compliant in this region. When the width of the slots decreases to zero the structure becomes much stiffer as indicated by the second much higher slope region of curve A. The amount of displacement associated with closing the slots is essentially indicated by point D where the slope of the Force/Displacement curve changes. Curve A indicates the behavior expected from forces applied at a point along compressive axis C, illustrating that a large amount of axial displacement follows from minimal compressive force on tubular member 290. Upon closing slots, the compressive axis becomes stiff (indicated by the large increase in Force at point D in the curve). Curve B in the graph indicates compression along the axis running through spine 308. Due to stress relief slots 306, a small amount of compressive displacement occurs before spine 308 stiffens and begins to act substantially like a solid tube, as indicated by point E in the graph. The structure will exhibit the behavior of curve B for tensional loads applied to the top of the structure on the compressive axis C as the gaps closed under this loading are very narrow. Curve B also represents the behavior of the structure to torsional loads, as the gaps impacted most by these loads are narrow.

Figure 18:
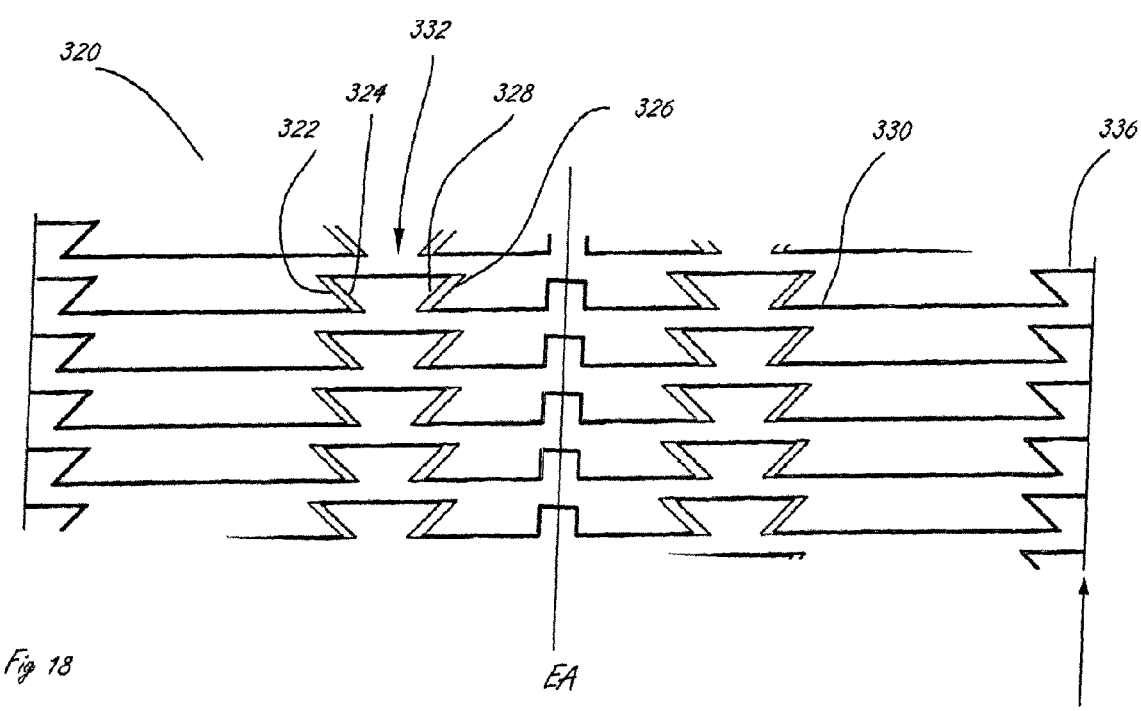
FIG. 18 illustrates a continuous cut pattern for use on a tubular member that is most steerable in tension.

FIG. 18 illustrates a flattened view of exemplary tubular member 320. Slot 330, or cut, formed therein has a spiral (also referred to herein as helical) pattern and is un-interrupted. Tubular member 320 is shown in an as-cut compressed configuration, and is adapted to be expanded the greatest amount along expansion axis EA upon the application of a tensile force thereto. Tubular member 320 includes interlocking features 332, which include surfaces 322 and 324, and surfaces 326 and 328. Slot 330 includes the slot defined by surfaces 326 and 328, and by surfaces 322 and 324. In this embodiment the slot, or gap, defined by surfaces 326 and 328 is larger than the gap defined by surfaces 322 and 324. That is, the gap that is closer to expansion axis EA is larger than the gap that is further from expansion axis EA. Tubular member 334 also includes spine 334, which is interrupted by small slots 336. As illustrated in FIG. 16c, tubular member 320, upon the application of axial loads applied thereto, will exhibit Force/Displacement curves as follows: a compressive force (downwards) applied at EA will exhibit curve B, while a tensile load at EA (upwards) will exhibit curve A. A torsional load will exhibit curve B.

Figure 19:
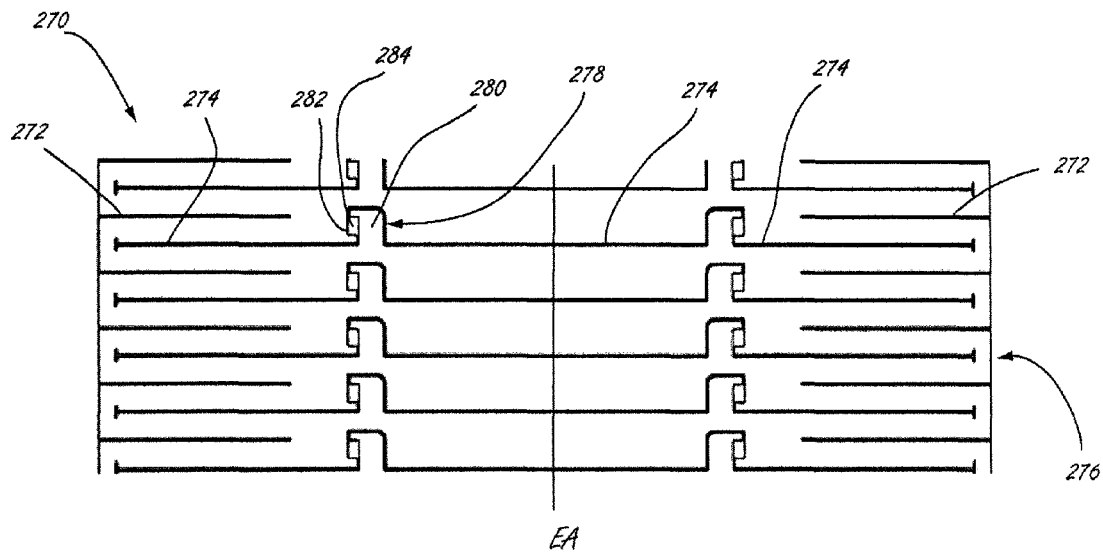
FIG. 19 illustrates a discontinuous cut pattern for use on a tubular member most steerable in tension.

FIG. 19 is a flattened view and illustrates a portion of a tubular member. Tubular member 270 can be an inner or an outer tubular member as described herein. Steerable portion 270 is a laser-cut tubular member wherein first cut, or slot, 274 is made to define spine 276. Cut 274 is made almost all the way around tubular member 270. Cut 274 also defines interlocking features 278 (only one of them is labeled), which are comprised of a first interlocking element 280 and a second interlocking element 282. Cut 274 includes cut 284, which creates the interlocking features and allows for movement between the two interlocking elements. Tubular member 270 also includes stress relief 272, which extend across spine 276 and provide stress relief for spine 276. Stress relief slots 272 can be considered to be axially in-between slots 274. Slots 274 are not connected with slots 272. Tubular member 270 is adapted to be expanded along expansion axis EA, and is adapted to be minimally compressible upon the application of compressive forces thereto. Spine 276 is substantially static. Upon the application of tensile forces to tubular member 270 along expansion axis EA, tubular member 270 will deflect from a straightened configuration into a bent configuration.

Figure 20:
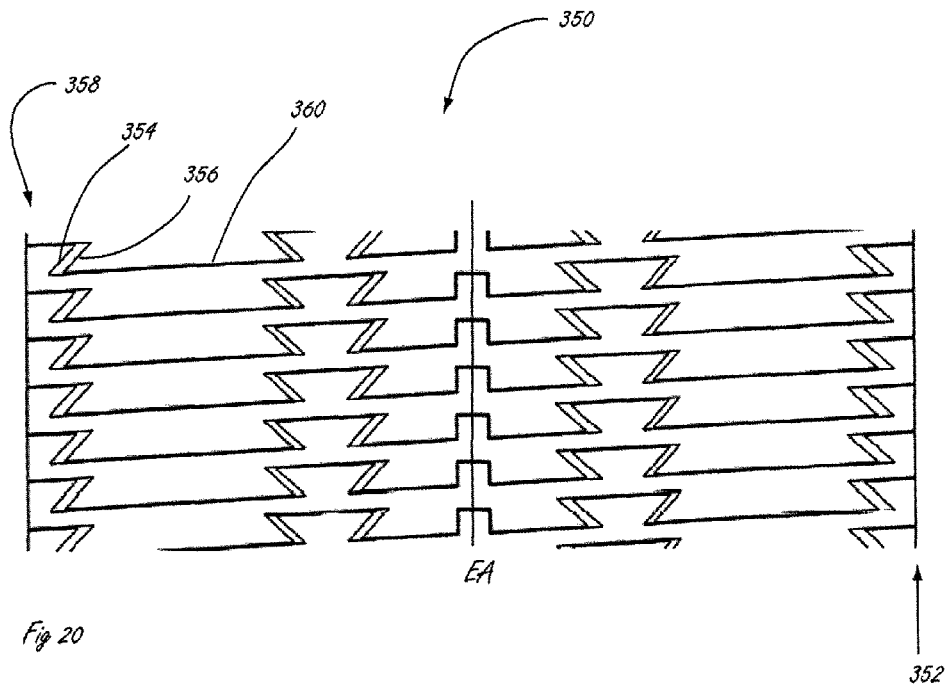
FIG. 20 illustrates a continuous cut pattern for use on a tubular member most deflectable in tension.

FIG. 20 illustrates an embodiment similar to that shown in FIG. 18 and only differences in the structure between the two will be described. All other features can be considered the same. Tubular member 350 includes interlocking features including interlocking elements 354 and 356. Slot 360 created in tubular member 350 includes the gap defined by surfaces of interlocking elements 354 and 356.

Figure 21:
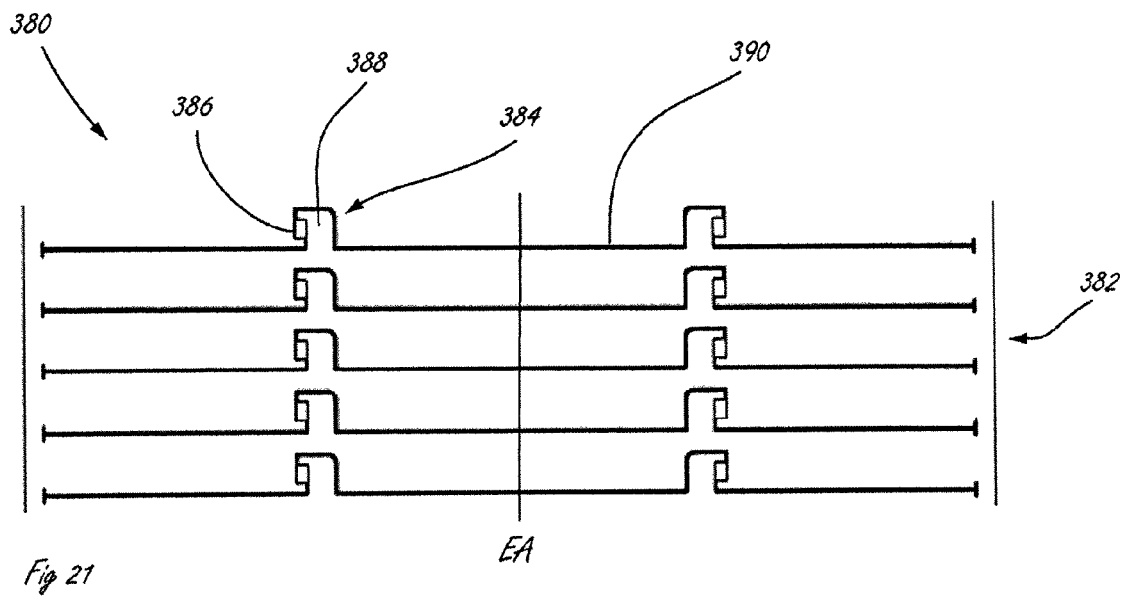
FIG. 21 illustrates a discontinuous cut pattern for use on a tubular member with a substantially straight, continuous spine.

FIG. 21 illustrates a flattened portion of an exemplary tubular member 380 including interrupted cuts 390 that define spine 382. Tubular member 380 includes interlocking features 384, which include interlocking elements 386 and 388. Interlocking features 384 allow for expansion along expansion axis EA upon the application of a tensile force thereto. Tubular member 380, like all tubular members described herein unless specifically stated otherwise, can be incorporated into a steerable portion as an inner or an outer tubular member.

Figure 22:
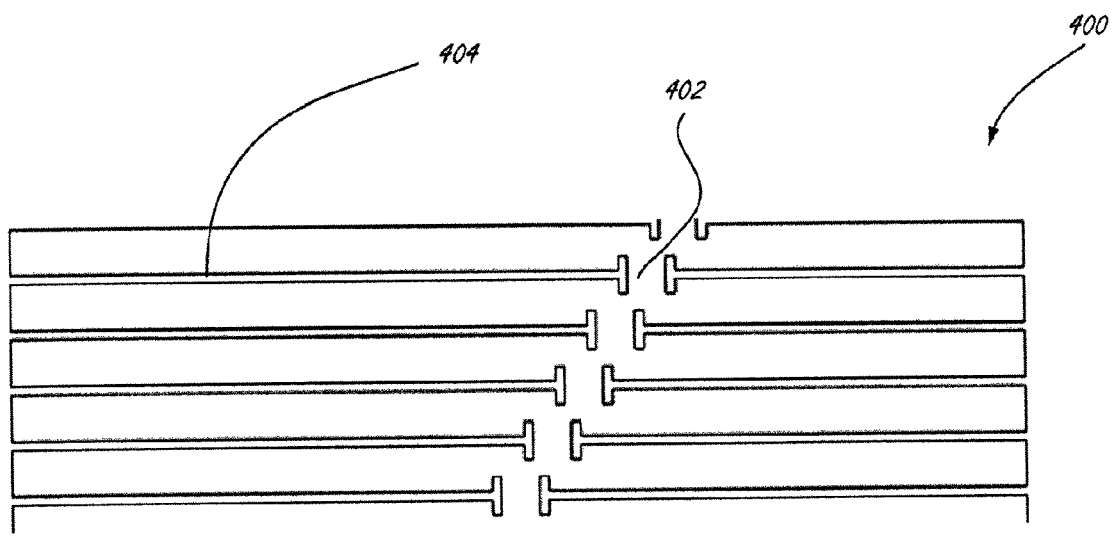
FIG. 22 illustrates a discontinuous cut pattern for use on a tubular member with a helical, continuous spine.

FIG. 22 illustrates a flattened portion of an exemplary tubular member 400. Interrupted slots 404 define spine 402, which has a spiral shape. Tubular member 400 does not have static axis.

FIG. 23 illustrates a flattened portion of an exemplary tubular member 410. Tubular member 410 includes interrupted helical slots 418, which define spines 412 and 414. Tubular member 410 has two spines, 180 degrees around the periphery of the device from one other. The helical cut pattern repeats itself every 180 degrees to define substantially straight spines. Tubular member 410 also includes a plurality of interlocking features 420 which provide torsional stiffness. The maximal expansion/compression is at axis 416.

FIG. 24 illustrates a flattened portion of an exemplary tubular member 430, which is similar to the embodiment in FIG. 23 but rather than repeating every 180 degrees, the cut pattern repeats every 360 degrees. Slots 434 have an interrupted helical design, and tubular member 430 has a single spine 432. Feature 436 provides additional torsional stiffness. Tubular member 430 exhibits maximal expansion/compression along axis 438.

FIG. 25 illustrates a flattened portion of an exemplary tubular member 440. Tubular member 440 includes slots 448, which repeat every 190 degrees to define spines 442 and 446. The slots have an interrupted helical pattern, and create a relatively neutral pattern.

FIG. 26 illustrates a flattened portion of an exemplary tubular member 450. Tubular member 450 has uninterrupted slot 456 formed therein, which repeats every 360 degrees. Tubular member 450 also includes interlocking features 454 comprised of at least two interlocking elements as described herein. In this embodiment, the interlocking elements have complimentary curved surfaces and are adapted to support rotation. Slot 456 defines spines 452, while slot 456 allows compression and/or expansion along axes A.

Figure 27:
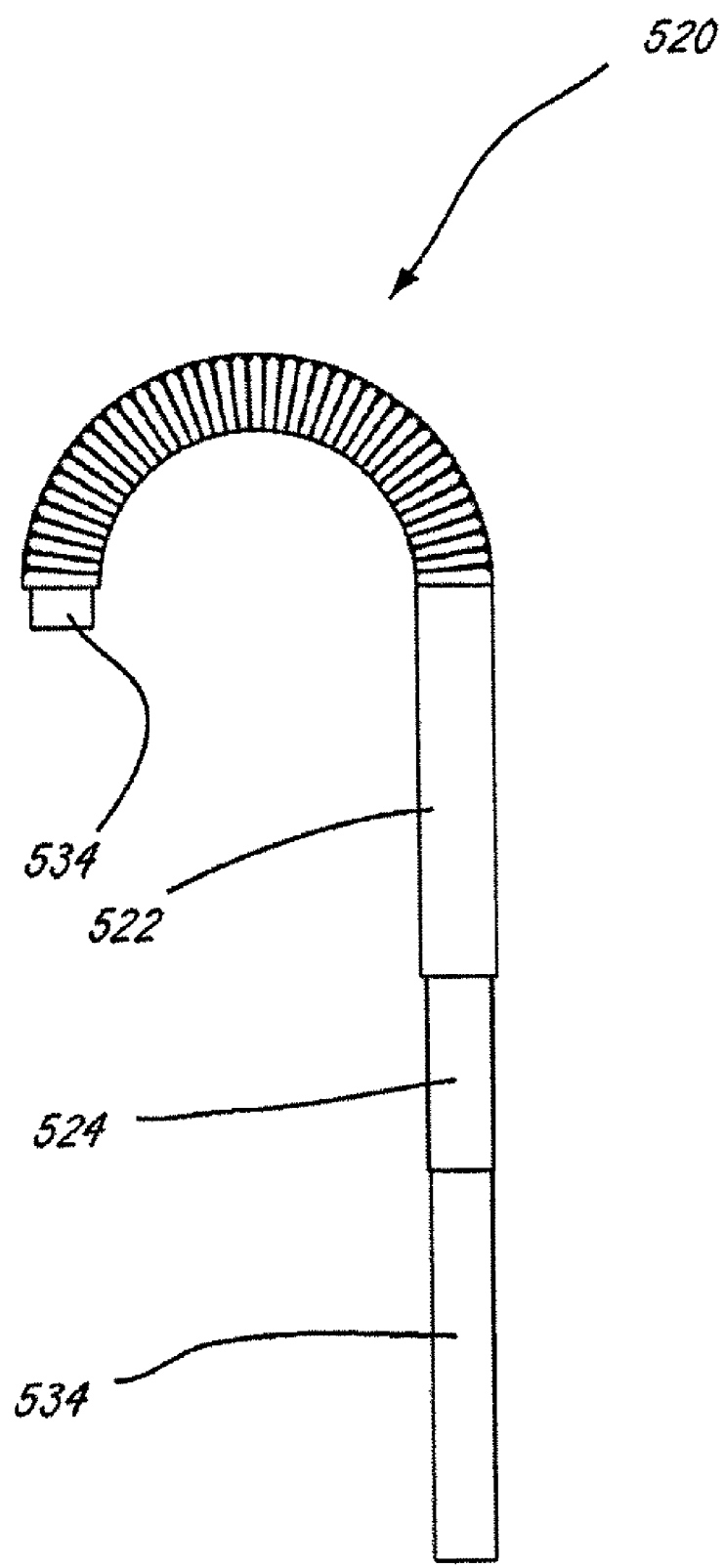
FIG. 27 illustrates an exemplary steerable delivery device including a floating tubular member disposed therein.

FIG. 27 illustrates an exemplary steerable delivery device including steerable portion 520. Steerable delivery device includes outer tubular member 522, inner tubular member 524, and floating inner member 534. Inner tubular member 524 is disposed within and coaxial to outer tubular member 522, and floating inner member 534 is disposed within and coaxial with inner tubular member 524. Floating inner member 534 is axially fixed relative to inner tubular member 524 at a location proximal to steerable portion 520. The device shown in FIG. 27 can also include a liner member disposed between the outer and inner tubular members.

Figure 28:
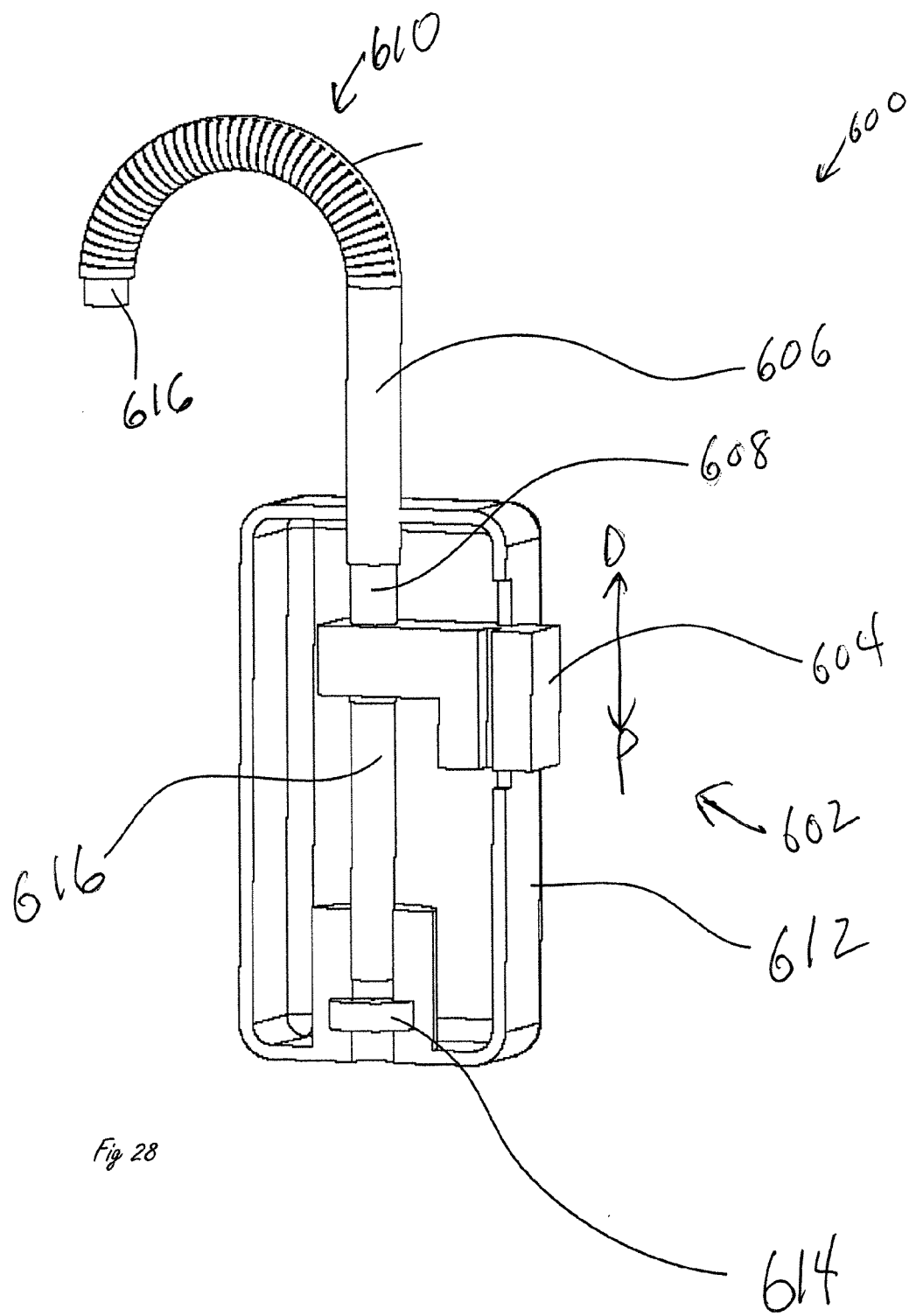
FIG. 28 illustrates an exemplary steerable medical delivery system.

FIG. 28 illustrates an exemplary steerable delivery system 600. System 600 includes control device 602 that is adapted to steer steerable portion 610 of a steerable delivery device. The steerable delivery device includes outer tubular member 606 and inner tubular member 608 disposed within outer tubular member 606. Control device 602 includes housing 612 with a slot therein adapted to allow for movement of actuator 604. Actuator 604 is coupled to inner tubular member 608, and is adapted to be moved axially, either distally D or proximally P to control the axial movement of inner tubular member 608. Any other suitable type of actuator can also be used including actuators incorporating mechanical advantage. Actuation of actuator 604 causes inner tubular member 608 to move axially relative to outer tubular member, which causes steerable portion 610 to bend. The control device is therefore adapted to steer steerable portion 610 inside of a subject. System 600 also includes a floating liner member 616 and hemostatic valve 614.

One aspect of the disclosure is a guide device that is adapted to be maintained, or locked, in a specific configuration to provide access for a medical device or instrument to be passed therethrough, but may or may not be steerable. In FIGS. 2A-2C, steerable portion 32 is adapted to be steered or deflected into any configuration between those shown in FIGS. 2A and 2B. Steerable portion is adapted to be steered to, for example, navigate bends or turns within a bodily lumen. In that specific embodiment, compressive and/or tensile forces are applied to the inner and/or outer tubular members to steer the steerable portion. In some embodiments, once steerable portion 32 is steered into a curved configuration, the forces applied thereto (e.g., compressive, tensile, torsional) can be released, and yet a medical device or instrument can be passed through the tubular members. In some embodiments, however, the bent configuration of the steerable portion can be maintained by maintaining the application of the forces thereto. For example, in FIGS. 2A-2C, steerable portion 32 can be maintained, or locked, in the bent configurations shown by maintaining the application of the compressive and/or tensile forces. By maintaining the application of the forces to the steerable portion or locking the relative displacements of the inner and outer tubes, the inner and outer tubes are substantially axially fixed relative to one another along the length of the steerable portion.

In an exemplary method of use, multiple bend portions may be incorporated and adapted to have a locked configuration that closely mimics, or resembles, a portion of the subject's anatomy. The bend portion can be advanced through the subject (e.g., over a guide wire) to a desired location, and can then be actuated into a curved configuration, such as by the application of compressive and/or tensile forces thereto. The curved configuration can be adapted to resemble the path of the anatomical lumen in which the device is positioned. Application of the actuation force maintains, or stiffens, the bend portions in the desired curved configuration. A medical device or instrument can then be advanced through the curved portion to a target location within the subject.

The device shown in FIG. 14 can alternatively be configured to be operated in this manner. For example, steerable delivery device 256 in FIG. 14 can be actuated to have a first bend or curved region 254 and a second bend or curved region 258. The curves, or bends, form a general S-shaped portion of the device. The delivery device 256 can be maintained, or locked, in the general S-shape to guide a medical device or instrument therethrough. The S-shape of the delivery device 256 can be used if it resembles a portion of the anatomy into which it is placed, but any other type of preformed configuration can be used, depending on the anatomical requirements. In the alternative to FIG. 14, the delivery device can be actuated into the configuration shown by the application of compressive and/or tensile forces to inner and outer tubular members, as is described herein.

Figure 29A:
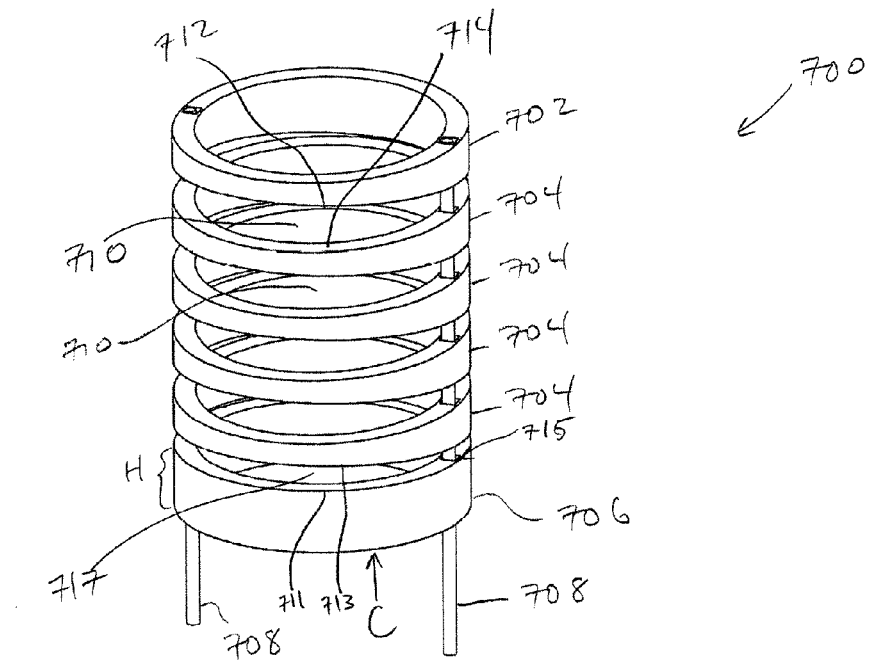
FIGS. 29A and 29B illustrate an exemplary embodiment of a lockable portion of a guiding device.
Figure 29B:
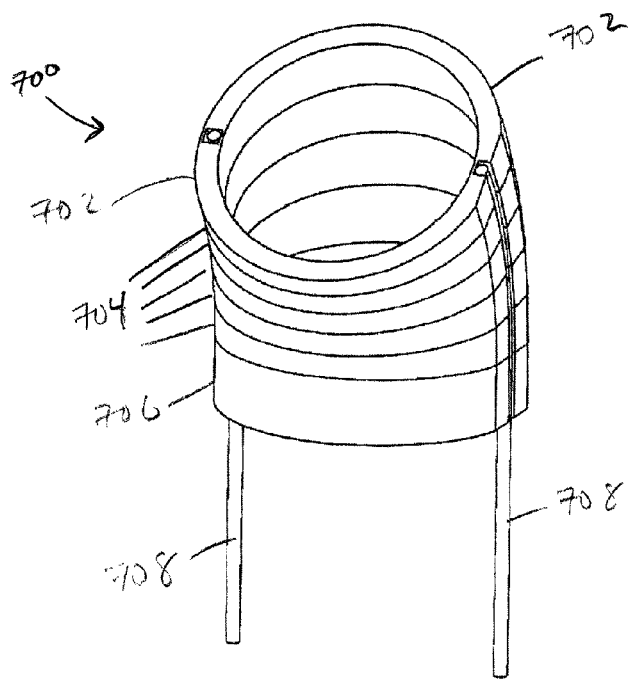

FIGS. 29A and 29B illustrate an exemplary embodiment of a portion of a lockable device adapted to be locked, or maintained, in a specific configuration that mimics that of a portion of the subject's anatomy. In the unlocked form the structure is compliant and easily guidable whereas in the locked form the device is rigid in its predetermined form. The device can then be used to provide access for a medical device or instrument to be passed therethrough to a target location within the subject. Bend portion 700 of the device includes a plurality of beads, 702, 704, and 706. Bead 702 is the distal-most bead, bead 706 is the proximal-most bead and beads 704 are disposed between the two end beads 702 and 706. The beads are separate and distinct structural features, not mechanically coupled to one another. Each bead has two bores 715 therethrough, each adapted to receive one of the two control wires 708. Control wires 708 are secured only to distal bead 702, using any suitable technique (e.g., adhesive). Wires 708 therefore are adapted to be axially moveable relative to beads 704 and 706. Proximal bead 706 has a substantially constant height H around the periphery of the bead, while beads 702 and 704 do not have a constant height. Specifically, the height of the beads 702 and 704 decreases around a portion of each of the beads. The gap between adjacent beads is therefore relatively large between bead 702 and 704, and between beads 704, while the gap between bead 706 and the adjacent bead 704 is relatively small compared to the other gaps.

To adjust the lockable portion into its predetermined form, an axially directed (i.e., distally directed) compressive force C is applied to proximal bead 706 while maintaining wires 208 is position. Maintaining wires 208 in position can occur based on a proximally directed tensile force applied to wires 208, or wires 208 may be secured to a portion of the delivery system that is not actuated. This causes the distance between surfaces 711 and 713 to decrease, until they engage one another as shown in FIG. 29B. The actuation force is continued until all of the beads' adjacent surfaces are engaged, as shown in the configuration in FIG. 29B. In FIG. 29B, lockable portion 700 is in a bent configuration adapted to mimic a portion of the patient's anatomy in which it is to be positioned. FIG. 29B also shows a section portion of one side of the beads through which one of wires 708 passes. Lockable portion is maintained in the locked configuration in FIG. 29B by maintaining the distally directed compressive force to proximal bead 706 or the relative displacements between distal bead 702 and proximal bead 706. Lockable portion 208 can also be bent into the configuration shown in FIG. 29B upon the application of a proximally directed tensile force applied to wires 708, while applying a distally directed compressive force to proximal bead 706. While six beads are shown in FIGS. 29A and 29B, the lockable portion can have two or more beads.

FIGS. 30A-30H show exemplary beads that can be incorporated into a lockable portion as described herein. FIG. 30A illustrates bead 716 with wire bores 717 therethrough. The height H of bead 716 is substantially constant. When the height is substantially constant, the planes through the proximal and distal ends of the beads are substantially parallel. When the height is not constant, the planes are not parallel. Bead 716 is the same as proximal bead 706 in FIG. 29A. In an embodiment with a lockable portion comprised entirely of beads that have a constant height, the lockable portion would have a straight configuration under compression. FIG. 30B shows bead 718 with bores therethrough, wherein the height at portion 720 is less than at portion 721. Bead 718 has the same general shape as beads 702 and 704 in FIG. 29A. The height of portion 720 can be adjusted to modify the curvature of the lockable portion. Generally, as height 720 decreases, the degree of the bend increases (i.e., the radius of curvature decreases). Similarly, the height of portion 721 can be modified to modify the curvature. FIG. 30C illustrates bead 722 that can be injection molded. Bead 722 includes two outer wire features 724 and two inner wire features 726 formed in bead 722. Each outer wire feature has a portion that overlaps with a portion the corresponding inner wire feature to define an opening through which a control wire can pass. Molding the bead with the wire features to create the wire bore can be easier than forming a hole the entire way through the bead. Bead 722 is formed to have 2 control wires pass therethrough. FIG. 30D illustrates bead 730 that can be injection molded. Bead 730 includes two indentations 732 and two indentations 734. The indentations in bead 730 allow for the height of wire bore 736 to be less than it would be without the indentations. The indentations can make the wire bores easier to mold. FIG. 30E illustrates bead 740 including tabs 742 stamped therein.

The tabs are stamped in the body of bead 740 to form wire openings 744, through which a control wire is passed. Bead 740 can be, for example, a hypotube, sheet metal rolled into an annular shape, etc. FIG. 30F is similar to FIG. 30E and includes interlocking features including interlocking elements 754 (male) and 756 (female). The interlocking features generally enhance torque transmission. The interlocking feature could be comprised of any interlocking elements described herein or any other suitable interlocking elements. FIG. 30G illustrates bead 760 including an inner corrugated member 764 and outer member 762. The spaces between inner member 764 and outer member 762 define control wire bores 768, which are adapted to receive control wires therethrough. In FIG. 30G, twelve control wires can be passed through bead 760. FIG. 30H shows a plurality of beads 760 (from FIG. 30G) and 770, each with inner member 764 and outer member 762. In adjacent beads 760 and 770, the control wire bores are defined by peaks and valleys formed in the inner members on adjacent beads.

While the embodiments have been shown with control wires being secured relative to a single bead, all of the control wires in a lockable portion need not be secured to the same bead. For example, a control wire can be secured to any bead in the lockable portion.

The locked configuration of the lockable portion can be modified by modifying characteristics of the beads. For example, the number of beads in the lockable portion can be modified to change the radius of curvature. The height of portion of the beads can be modified, as shown in the comparison between FIGS. 30A and 30B. The lockable portion additionally need not include beads of the same type. For example, a lockable portion could alternate the beads shown in FIGS. 30A and 30B, creating a curve with a degree of bend less than that shown in FIG. 29A. Beads of similar design can be rotationally offset from one another along the length of the lockable portion. For example, in the embodiment in FIG. 29A, every other bead could be rotated 90 degrees in the same direction relative to the adjacent beads. Additionally, the relative angle between the control wire bore axis and the plane of a bead end can be adjusted. For example, in FIG. 30B, the axes of control wire bores 719 can be substantially 90 degrees relative to the plane of the distal end of bead 718. The axes of bores 719, can, however, be offset such that they are not substantially 90 degrees relative to the plane of the distal end of bead 718.

The beads as described herein can have almost any length. In some embodiments a bead is a section of straight tubing. Any bead can also incorporate any of the slotted cut patterns described herein While the lockable portions have been shown to include curved, or bent sections, the lockable device can have a locked configuration in which the device is substantially straight. For example, if the lockable device included 2 or more beads as shown in FIG. 30A, the lockable device would have a substantially straight locked configuration.

In some embodiments the lockable device could have a floating liner (as described herein) disposed therein. The floating liner could, in some embodiments, secured to the distal-most bead. The lockable device could alternatively or additionally have an outer liner disposed on the outside of the lockable device. The outer liner could also be secured to the distal-most bead or the outer liner could be affixed to the inner liner and the beads left to float inside.

In some embodiments the lockable device (e.g., the device shown in FIGS. 29A and 29B) is adapted to be advanced over a steerable device within the subject. For example, a traditional guidewire or the steerable device shown in FIGS. 2A-2C can be steered to a desired location within the subject. A lockable device, such as a beaded lockable device described herein, can then be tracked over the steered device. The lockable device comprising at least two beads is flexible to allow it to follow the curvature of the steered device. Once the lockable device has been advanced over the steered device to the desired position, the beads of the lockable device are locked in place as described herein, and the lockable device assumes its preset configuration.

In alternative embodiments, the lockable portion (e.g., the beaded structure in FIGS. 29A and 29B) includes a floating liner therein.

In an exemplary embodiment of use, a guiding element (e.g., a guidewire) is advanced to a desired location within the subject. The device comprising the lockable portion is then tracked over the guiding element until it reaches a desired position. The lockable portion is then actuated to change the configuration of the lockable portion to the desired configuration. The lockable portion is then maintained, or locked, in the desired configuration. A medical device, medical instrument, or other device is then advanced therethrough to a target location within the subject.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. The following claims define the scope of the disclosure and that methods and structures within the scope of these claims and their equivalents are covered thereby.

What is claimed is:

1. A steerable medical delivery device, comprising:
a steerable portion comprising a first tubular member and a second tubular member, wherein one of the first and second tubular members is disposed within the other, wherein the first and second tubular elements are permanently axially fixed relative to one another at a fixation location distal to the steerable portion, and wherein the first and second tubular members are axially movable relative to one another along the steerable portion to steer the steerable portion in a first direction, and
wherein the first tubular member is adapted to preferentially bend in a first direction.

2. The device of claim 1 wherein the second tubular member is substantially uniform and is not adapted to preferentially bend.

3. The device of claim 1 wherein the first tubular member comprises at least one slot therein to define a first spine.

4. The device of claim 3 wherein the second tubular member comprises at least one slot therein to define a second spine.

5. The device of claim 1 wherein the first tubular member comprises a braided material.

6. The device of claim 1 wherein the first tubular member is disposed within the second elongate tubular member.

7. The device of claim 1 wherein the first tubular member is adapted to be moved axially relative to the second tubular member to apply one of a compressive force and a tensile force to the first tubular member and the other of the compressive force and the tensile force to the second tubular member to steer the steerable portion in a first direction.

8. The device of claim 1 wherein the second tubular member is adapted to preferentially bend in a second direction.

9. The device of claim 8 wherein the first direction is substantially opposite the second direction.

10. The device of claim 1 wherein the second elongate tubular element is a floating tubular member.

11. A steerable medical delivery device, comprising:
a steerable portion comprising an outer tubular member and an inner tubular member, wherein the inner tubular member is disposed radially within the outer tubular member,
wherein the outer tubular member includes at least one outer slot therein to define an outer spine, and
wherein the outer tubular member and the inner tubular member are axially movable relative to one another along the steerable portion and are axially fixed relative to one another at a location distal to the steerable portion,
wherein the outer slot includes a first interlocking element and a second interlocking element each adapted to allow relative movement therebetween when in a first configuration and each further adapted to prevent movement therebetween at least along a first axis when in a second configuration.

12. The device of claim 11 wherein the outer tubular member comprises a plurality of discontinuous slots to define the outer spine.

13. The device of claim 11 wherein the inner tubular member comprises a plurality of discontinuous slots to define the inner spine.

14. The device of claim 11 wherein the inner and outer spines are offset substantially 180 degrees from one another.

15. The device of claim 11 wherein the inner and outer spines are adapted to receive one of a compressive force and a tensile force to steer the steerable portion of the delivery device.

16. The device of claim 15 wherein the inner spine is adapted to receive a compressive force thereto and the outer spine is adapted to receive a tensile force thereto to steer the steerable portion of the delivery device in a first direction.

17. The device of claim 15 wherein the inner spine is adapted to receive a tensile force thereto and the inner spine is adapted to receive a compressive force thereto to steer the steerable portion of the delivery device in a first direction.

18. The device of claim 11 wherein the inner and outer slots are in substantial alignment relative to a longitudinal axis of the steerable portion when the steerable portion is in a straightened configuration.

19. The device of claim 18 wherein the inner and outer slots are substantially perpendicular to the longitudinal axis of the steerable portion when the steerable portion is in a straightened configuration.

20. The device of claim 11 wherein the inner and outer slots are not in alignment relative to a longitudinal axis of the steerable portion when the steerable portion is in a straightened configuration.

21. The device of claim 11 wherein the inner tubular member includes at least one inner slot therein to define an inner spine, the inner and outer spines being offset relative to one another, wherein the inner slot includes a first interlocking element and a second interlocking element each adapted to allow relative movement therebetween when in a first configuration and each further adapted to prevent movement therebetween when in a second configuration.

22. The device of claim 11 wherein the delivery device further comprises a fixation element distal to the steerable portion adapted to prevent axial movement between the outer tubular element and the inner tubular element.

23. The device of claim 11 wherein the inner tubular member has an inner surface, and wherein the inner surface is sized to allow a medical device to be advanced therethrough.

24. A steerable medical delivery device, comprising:
an elongate member comprising a distal end, a proximal end, and a steerable portion adapted to be steered in a first direction, wherein the distal end is adapted to be inserted into a subject; and
a floating element disposed within the steerable portion, wherein the floating element is axially fixed relative to the elongate member at a location proximal to the steerable portion, and is not axially fixed relative to the elongate member along the steerable portion.

25. The device of claim 24 wherein the elongate member is a catheter.

26. The device of claim 24 wherein the elongate member comprises an inner tubular member with an inner slot therein to define a first spine, and an outer tubular member with an outer slot therein to define an outer spine, wherein the spines are offset from one another.

27. The device of claim 11 wherein the outer tubular member and the inner tubular member are permanently axially fixed relative to one another at a location distal to the steerable portion.

28. A steerable medical delivery device, comprising:
a steerable portion comprising an outer tubular member and an inner tubular member, wherein the inner tubular member is disposed radially within the outer tubular member,
wherein the outer tubular member includes at least one outer slot therein to define an outer spine,
wherein the outer tubular member and the inner tubular member are axially movable relative to one another along the steerable portion and are permanently axially fixed relative to one another at a location distal to the steerable portion,
wherein the outer slot includes a first interlocking element and a second interlocking element each adapted to allow relative movement therebetween when in a first configuration and each further adapted to prevent movement therebetween at least along a first axis when in a second configuration.

29. The device of claim 28 wherein the inner tubular member includes at least one inner slot therein to define an inner spine, the inner and outer spines being offset relative to one another, and wherein the inner slot includes a first interlocking element and a second interlocking element each adapted to allow relative movement therebetween when in a first configuration and each further adapted to prevent movement therebetween at least along a first axis when in a second configuration.

30. A steerable medical delivery device, comprising:
a steerable portion comprising a first tubular member and a second tubular member, wherein one of the first and second tubular members is disposed within the other, wherein the first and second tubular elements are permanently axially fixed relative to one another at a fixation location distal to the steerable portion, and wherein the first and second tubular members are adapted to be axially moved relative to one another along the steerable portion to steer the steerable portion in a first direction.

31. The device of claim 30 wherein the first tubular member is adapted to preferentially bend in a first direction.

32. A steerable medical delivery device, comprising:
a steerable portion comprising a first tubular member and a second tubular member, wherein one of the first and second tubular members is disposed within the other, wherein the first and second tubular elements are permanently axially fixed relative to one another at a fixation location distal to the steerable portion, and wherein the first and second tubular members are adapted to be axially moved relative to one another along the steerable portion to steer the steerable portion in a first direction; and an external controller adapted to axially displace the first and second tubular members relative to one another to steer the steerable portion in the first direction.

33. The device of claim 32 wherein the controller is adapted to be disposed external to a patient.

34. The device of claim 32 wherein the controller is mechanically coupled to one of the first and second tubular members and is adapted to move one of the first and second tubular members upon actuation of the controller.

* * * * *